(12) United States Patent
Satcher, Jr. et al.

(10) Patent No.: US 6,682,938 B1
(45) Date of Patent: Jan. 27, 2004

(54) GLUCOSE SENSING MOLECULES HAVING SELECTED FLUORESCENT PROPERTIES

(75) Inventors: Joe H. Satcher, Jr., Modesto, CA (US); Stephen M. Lane, Oakland, CA (US); Christopher B. Darrow, Pleasanton, CA (US); Douglas R. Cary, Oakland, CA (US); Joe Anh Tran, Livermore, CA (US)

(73) Assignees: The Regents of the University of California, Oakland, CA (US); Minimed Inc., Sylmar, CA (US)

( * ) Notice: Subject to any disclaimer, the term of this patent is extended or adjusted under 35 U.S.C. 154(b) by 459 days.

(21) Appl. No.: 09/663,567

(22) Filed: Sep. 15, 2000

Related U.S. Application Data

(60) Provisional application No. 60/154,103, filed on Sep. 15, 1999.

(51) Int. Cl.[7] ............................................. G01N 33/00
(52) U.S. Cl. ........................................... 436/172; 568/1
(58) Field of Search ............................... 568/1; 436/172

(56) References Cited

U.S. PATENT DOCUMENTS

| | | |
|---|---|---|
| 4,401,122 A | 8/1983 | Clark, Jr. |
| 4,428,366 A | 1/1984 | Findl et al. |
| 4,496,722 A | 1/1985 | Gallop et al. |
| 4,655,225 A | 4/1987 | Dahne et al. |
| 4,680,268 A | 7/1987 | Clark, Jr. |
| 4,805,623 A | 2/1989 | Jobsis |
| 4,861,728 A | 8/1989 | Wagner |
| 4,875,486 A | 10/1989 | Rapoport et al. |
| 4,882,492 A | 11/1989 | Schlager |
| 4,924,009 A | 5/1990 | Neckers et al. |
| 4,974,929 A | 12/1990 | Curry |
| 5,028,787 A | 7/1991 | Rosenthal et al. |
| 5,054,487 A | 10/1991 | Clarke |

(List continued on next page.)

FOREIGN PATENT DOCUMENTS

| | | |
|---|---|---|
| EP | 0 693 271 A1 | 7/1994 |
| EP | 0 729 962 A1 | 3/1995 |

(List continued on next page.)

OTHER PUBLICATIONS

Okafor, C.O., "Synthesis, Properties and Uses of Angular Phenoxazines," *Dyes and Pigments*, Elsevier Applied Science Publishers Ltd., England, vol. 7, No. 2, 1986, pp. 103–131, XP–002122264.

(List continued on next page.)

*Primary Examiner*—Jill Warden
*Assistant Examiner*—Monique T. Cole
(74) *Attorney, Agent, or Firm*—Gates & Cooper LLP

(57) ABSTRACT

An analyte sensing fluorescent molecule that employs intramolecular electron transfer is designed to exhibit selected fluorescent properties in the presence of analytes such as saccharides. The selected fluorescent properties include excitation wavelength, emission wavelength, fluorescence lifetime, quantum yield, photostability, solubility, and temperature or pH sensitivity. The compound comprises an aryl or a substituted phenyl boronic acid that acts as a substrate recognition component, a fluorescence switch component, and a fluorophore. The fluorophore and switch component are selected such that the value of the free energy for electron transfer is less than about 3.0 kcal mol$^{-1}$. Fluorescent compounds are described that are excited at wavelengths greater than 400 nm and emit at wavelengths greater than 450 nm, which is advantageous for optical transmission through skin. The fluorophore is typically selected from transition metal-ligand complexes and thiazine, oxazine, oxazone, or oxazine-one as well as anthracene compounds. The fluorescent compound can be immobilized in a glucose permeable biocompatible polymer matrix that is implantable below the skin.

24 Claims, 21 Drawing Sheets

U.S. PATENT DOCUMENTS

| | | |
|---|---|---|
| 5,070,874 A | 12/1991 | Barnes et al. |
| 5,077,476 A | 12/1991 | Rosenthal |
| 5,086,229 A | 2/1992 | Rosenthal et al. |
| 5,101,814 A | 4/1992 | Palti |
| 5,112,124 A | 5/1992 | Harjunmaa et al. |
| 5,137,833 A | 8/1992 | Russell |
| 5,196,709 A | 3/1993 | Berndt et al. |
| 5,203,328 A | 4/1993 | Samuels et al. |
| 5,235,045 A | 8/1993 | Lewis et al. |
| 5,246,867 A | 9/1993 | Lakowicz et al. |
| 5,279,543 A | 1/1994 | Glikfeld et al. |
| 5,281,825 A | 1/1994 | Berndt et al. |
| 5,308,773 A | 5/1994 | Lewis et al. |
| 5,342,789 A | 8/1994 | Chick et al. |
| 5,353,790 A | 10/1994 | Jacques et al. |
| 5,362,307 A | 11/1994 | Guy et al. |
| 5,409,835 A | 4/1995 | Lakowicz et al. |
| 5,445,611 A | 8/1995 | Eppstein et al. |
| 5,458,140 A | 10/1995 | Eppstein et al. |
| 5,476,094 A | 12/1995 | Allen et al. |
| 5,495,850 A | 3/1996 | Zuckerman |
| 5,503,770 A | 4/1996 | James et al. |
| 5,512,246 A | 4/1996 | Russell et al. |
| 5,628,310 A | 5/1997 | Rao et al. |
| 5,763,238 A | 6/1998 | James et al. |
| 6,002,954 A | 12/1999 | Van Antwerp et al. |
| 6,040,194 A | 3/2000 | Chick et al. |
| 6,344,360 B1 | 2/2002 | Colvin et al. |

FOREIGN PATENT DOCUMENTS

| | | |
|---|---|---|
| EP | 0 673 622 A3 | 9/1995 |
| FR | 2 253 794 | 7/1975 |
| WO | WO 82/01804 | 5/1982 |
| WO | WO 91/18912 | 12/1991 |
| WO | WO 96/03074 | 2/1996 |
| WO | WO 97/19188 | 5/1997 |
| WO | WO 97/29154 | 8/1997 |
| WO | WO 98/22820 | 5/1998 |
| WO | WO 99/46600 | 9/1999 |
| WO | WO 01/18543 | 3/2001 |
| WO | WO 02/054067 | 7/2002 |

OTHER PUBLICATIONS

Xuhong, Qian et al., "The Synthesis, Application and Prediction of Stokes Shift in Fluorescent Dyes Derived from 1,8–Naphthalic Anhydride," *Dyes and Pigments*, Elsevier Applied Science Publishers Ltd., England, vol. 11, No. 1, 1989, pp. 13–20, XP–000026521.

J. Yoon et al., "Fluorescent Chemosensors . . . Quenching," J. Am. Chem. Soc., 1992, 114:5874–5875.

L.K. Mohler et al., "α–Amino Acid Chelative . . . Acid," J. Am. Chem. Soc., 1993, 115:7037–7038.

A.W. Czarnik, "Chemical Communication . . . Chemosensors," Acc. Chem. Res., 1994, 27:302–308.

K.r.A. Samankumara Sandanayake et al., "Molecular Fluorescence Sensor for . . . Coumarin," Chemistry Letters, 1995, pp. 139–140.

J. Joon et al., "Fluorescent chemosensors . . . found," SPIE, 1992, vol. 1796, pp. 87–91.

T.D. James et al., "Novel Photoinduced Electron–transfer . . . Amine," J. Chem. Soc. Chem. Commun., 1994, pp. 47–48.

D. Monroe, "Novel implantable glucose sensors," ACL, 1989, pp. 8–16.

J.R. Lakowicz, et al., "Emerging Biomedical and Advanced Applications . . . Spectroscopy," Journal of Fluorescence, 1994, 4(1):117–136.

D.A. Gough et al., "Development of the Implantable Glucose Sensor," Diabetes, 1995, 44:1005–1009.

M.A. Arnold et al., "Determination of Physiological Levels . . . Spectra," Anal. Chem., 1990, 62:1457–1464.

D.T. Bostick et al., "Quantitative Determination of Blood . . . Luminol," Anal. Chemistry, 1975, 47(3):447–452.

"The Effect of Intensive Treatment . . . Mellitus," The New England Journal of Medicine, 1993, 329(14):977–986.

A. Falasca et al., "Purification and Partial . . . Sativa," Biochimica et Biophysica Acta, 1979, 577:71–81.

G.G. Guilbault et al., "Homovanillic Acid as a . . . Enzymes," Analytic Chemistry, 1968, 40(1):190–196.

A. Indelli et al., "Salt Effects in the Reaction . . . Ions," Journal of the American Chemical Society, 1960, 82(13):3233, 3863–3866.

T.D. James, et al., "Novel Saccharide–Photoinduced . . . Amine," J. Am. Chem. Soc., 1995, 117:8982–8987.

T.D. James et al., "Chiral discrimination of . . . sensor," Nature, 1995, 374:345–347.

J.R. Lakowicz et al., "Fluorescence lifetime–based sensing . . . glucose," Sensors and Actuators B, 1993, 11:133–143.

D.S. Kemp et al., "Synthesis of Cyclophanes . . . methylnaphthalenes," The Journal of Organic Chemistry, 1979, 44(25):4700–4703.

K. Nakashima et al., "Sugar–Assisted Chirality . . . Complexes," Chemistry Letters, 1994, pp. 1267–1270.

L.A. Marquardt et al., "Near–Infrared Spectroscopic . . . Matrix," Anal. Chem., 1993, 65:3271–3278.

D. Pilosof et al., "Microporous Membrane Flow . . . Glucose," Anal. Chem., 1982, 54:1698–1701.

G.S. Wilson, "Can Continuous Glucose . . . Diabetes," Anal. Chem., 1992, 64(6):381–386.

M. Uziel et al., "Direct Labeling of DNA . . . Group," Biochemical and Biophysical Research Communications, 1991, 180(3):1233–1240.

Burnett, Thomas J. et al., "Biochemical and Biophysical Research Communications", Academics Press, Inc., vol. 96, No. 1, Sep. 16, 1980, pp. 157–162.

R¹ = -(CH₂)₃CH₃ (a), -(CH₂)₅OH (b), -(CH₂)₅O(THP) (c)
R² = Cl (x), Me (y), H (z)

GLUCOSE SENSING MOLECULES HAVING SELECTED FLUORESCENT PROPERTIES

This application claims the benefit of United States provisional patent application serial No. 60/154,103, filed Sep. 15, 1999. The entire content of this provisional patent application is incorporated herein by reference.

This application is related to the following co-pending and commonly-assigned patent applications:

U.S. patent application Ser. No. 09/461,627 "DETECTION OF BIOLOGICAL MOLECULES USING BORONATE BASED CHEMICAL AMPLIFICATION AND OPTICAL SENSORS", by William Van Antwerp et al., filed on Dec. 14, 1999, which is a Continuation of U.S. patent application Ser. No. 08/749,366, now U.S. Pat. No. 6,002,954 which claims the benefit of U.S. Provisional Patent Application Serial No. 60/007,515, filed Nov. 22, 1995; and U.S. patent application Ser. No. 09/078,392 "DETECTION OF BIOLOGICAL MOLECULES USING CHEMICAL AMPLIFICATION AND OPTICAL SENSORS", by William Van Antwerp et al., filed on Nov. 21, 1999, which is a Continuation of U.S. patent application Ser. No. 08/752,945, now U.S. Pat. No. 6,011,984, which is a Continuation-in-Part of U.S. patent application Ser. No: 60/007,515 and is related to U.S. Ser. No. 08/721,262, filed Sep. 26, 1996, now U.S. Pat. No. 5,777,060, which is a Continuation-in-Part of U.S. Ser. No. 08/410,775, filed Mar. 27, 1995, now abandoned; the complete disclosures of each of these related applications being incorporated herein by reference.

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

This invention relates to the design of fluorescent compounds used as glucose sensors that have selected fluorescent properties, such as long fluorescence lifetimes, long absorption or emission wavelengths, or high quantum yields. More particularly, the invention relates to biomedical sensors for continuous transdermal optical transduction of tissue glucose concentration for the treatment of diabetes.

2. Description of Related Art

Molecular recognition coupled with fluorescent quenching is a promising analytical technique for optical transduction of analyte concentrations in bioassays. Several schemes employing fluorescent resonant energy transfer (FRET) have been proposed. Intramolecular electron transfer schemes, also called photoinduced electron transfer or PET, appear superior from the standpoint of chemical robustness and simplicity.

U.S. Pat. No. 5,503,770 to James et al. discloses a fluorescent compound used for the detection of saccharides or sugars such as glucose. The use of these fluorescent compounds was extended in U.S. Pat. No. 6,002,954 to Van Antwerp et al., by incorporating the compounds in an implantable optical sensor for transduction of glucose concentration for the treatment of diabetes. The fluorescent transducer is implanted 1–3 mm below the surface of the skin and optically interrogated externally to determine the level of tissue glucose in diabetic patients. A minimally-invasive, continuous glucose sensor is of great benefit to patients in achieving tighter blood-glucose control when combined with existing insulin pumps.

One of the systems described in U.S. Pat. No. 6,002,954 is made of anthracene boronate, which is excited at about 380 nm and emits at about 420 nm. Unfortunately, excitation and fluorescent emission at wavelengths in the range of about 360–420 nm is only weakly transmitted through skin. The light transmission through the skin must be significantly increased for the molecule to be useful as a sensor over the clinically relevant range of tissue glucose concentration. In addition, it may also be advantageous to modify other properties of the system associated with the fluorescent portion of the sensing molecule. Such properties may include the quantum yield, the fluorescence lifetime, photostability, chemical stability, and biocompatibility.

To improve transmission of the signal through the skin, the fluorescent compound should operate at longer wavelengths than about 450 nanometers. The transmission through a few millimeters of skin increases logarithmically with wavelength—from 0.1% at about 400 nm to almost 100% at 850 nm. Thus, the longer the wavelength, the greater the transmission through skin. An excitation and emission wavelength greater than about 600–650 nm is an enormous improvement over about 400–450 nm. Because of the significant increase in optical skin transmission at longer wavelengths, a practical glucose sensor can operate more efficiently, more accurately, and with a greater signal-to-noise ratio.

In addition, it is advantageous to match the peak excitation wavelength with an existing light source (such as an LED or diode laser). Furthermore, by operating at longer wavelengths, there is a reduction in the tissue autofluorescence background. Further progress in creating such compounds, however, entails the formidable task of synthetically assembling various combinations of fluorophores and glucose-recognizers into integrated molecules that have the desired fluorescent properties, such as operating at longer wavelengths (450–700 nm), while simultaneously retaining the requisite glucose transduction properties.

This invention addresses the optical transmission problem and provides exemplary fluorescent compounds that have been demonstrated to exhibit the needed photochemical behavior and operate in a wavelength range that makes a subcutaneous fluorescent glucose sensor practical.

SUMMARY OF THE INVENTION

The invention disclosed herein provides fluorescent analyte binding compounds defined by a specified formula and wherein substituent molecules of these compounds are selected to have complimentary molecular properties which can be determined via simplified version of the Rehm-Weller equation. The representative molecules of the invention have a number of exceptional activities that make them uniquely suited for incorporation into a sensor for analytes such as sugars. These activities include highly desirable fluorescent properties such as longer excitation and emission wavelengths, properties which are highly compatible with their use in minimally implantable systems for the continuous transdermal monitoring of blood glucose concentrations.

As shown by the disclosure provided herein, it is an object of the present invention to provide fluorescent compounds that may be incorporated into a sensor for saccharides or sugars and that have desired fluorescent properties, such as longer absorption or emission wavelengths, high quantum yields, or long fluorescence lifetimes. It is an object of the present invention to provide glucose sensing fluorescent molecules that operate at emission wavelengths greater than about 450 nm. It is another object of the present invention to provide glucose sensing fluorescent molecules that operate at excitation wavelengths greater than about 400 nm. The sensors can then be used to sense glucose concentrations in media with high visible blue and ultraviolet opacities such as human tissue.

Another object of the invention is to provide a sensor comprising a biocompatible polymer containing covalently bonded fluorescent molecules that specifically and reversibly bind glucose. Upon binding with the glucose, the fluorescence quantum yield of the molecules is increased, resulting in increased fluorescent emission at increasing glucose concentrations. Glucose transduction is achieved at wavelengths that allow the sensor to be implanted subcutaneously and permit improved optical transmission through skin.

The invention basically involves a fluorescent compound having three functional components in one molecule: a substrate-recognition component (typically a substituted aryl boronic acid), a fluorescence "switch" that is mediated by a substrate recognition event (typically an amine), and a fluorophore. The sensor molecule is designed so that the photo-excited fluorophore and the boron atom compete for the unbonded amine electrons. In the absence of glucose binding, electron transfer occurs predominantly with the fluorophore, causing fluorescent quenching and subsequently weak emission. When glucose is bound to the boronate group, the average charge on the boron atom becomes more positive, which increases the attraction of the unbonded electrons, preventing electron transfer, thus disabling the fluorescent quenching, and therefore causing strong emission.

Achieving successful interplay of these molecular components, resulting in optochemical glucose sensitivity, requires a precise matching of their electrochemical and photophysical properties. For example, given a functioning glucose-sensor molecule, shifting the wavelength of operation cannot be accomplished by simply substituting the original fluorophore with another fluorophore of the desired wavelength. Rather, a fluorophore and a switch with compatible reduction and oxidation potentials and photo-excited state energy must be selected. Similarly, other modifications of the molecule, such as to accommodate immobilization of the molecule in a biocompatible substrate (suitable for surgical implantation), could alter the oxidation potential of the 'switch' component, thereby upsetting the electrochemical balance required for operation. Therefore, modifications, variations or substitutions of these three components must be evaluated both electrochemically and optochemically so that compatibility can be established prior to the often lengthy process of synthetically incorporating them into a new molecular system. Experimental measurements were carried out for the purpose of screening prospective components and for evaluating the opto-chemical glucose sensitivity of compounds synthetically derived from those components.

When these components are assembled into the final sensor molecule, interactions between the assembled components are easily capable of modifying both the electrochemical potentials and photophysical characteristics of the stand-alone components. Surprisingly, it was found that for the boronate glucose sensing molecule having the specific formula described in this application, these interactions are minimal. Therefore, measurements made on the individual components such as the specific fluorophore afford an accurate prediction of the PET behavior of the final assembled molecule. Consequently, a simplified version of the Rehm-Weller equation can be employed to identify saccharide binding fluorescent compounds having the desired activities so that they can be synthesized for a variety of applications.

Glucose transduction has been successfully achieved by three typical classes of candidate molecules that were investigated: transition metal-ligand boronate compounds and conjugated organic heterocyclic ring system compounds that are oxazine, oxazine-one, oxazone, and thiazine boronate compounds and anthracene boronate compounds. Typically, these compounds are excited at wavelengths greater than about 400 nm. In addition, these compounds typically operate (emit) at wavelengths greater than about 450 nm.

The present invention is thus useful in the detection, localization, and quantification of saccharide or sugar concentration in media that are opaque in the visible blue or ultraviolet spectral regions. A glucose sensor according to the present invention can be incorporated into a minimally invasive, implantable system for continuous transdermal monitoring of glucose levels in diabetic patients. In addition, glucose sensors can be designed having other desired molecular properties, such as a longer fluorescence lifetime, specific excitation and emission wavelengths, high quantum yields, photostability, chemical stability, high water solubility, low temperature sensitivity, or low pH sensitivity.

Although the sensor molecules for sugars like glucose are of primary interest for biomedical applications, the present sensor/transducer scheme is useful more generally for the measurement of any cis-diol. For example, the present sensor molecules have utility in the measurement of ethylene glycol contamination in boiler waters, where ethylene gycol contamination is an indication of heat exchanger tube degradation. These sensor molecules, in addition to being used as glucose sensor molecules for diabetics, can be of use in industrial fermentation processes (e.g. beer and wine), or in any number of process points in the production of high fructose corn syrup (e.g. enzyme reactors). Other objects, features, and advantages of the present invention will become apparent from the following description and accompanying drawings.

BRIEF DESCRIPTION OF THE DRAWINGS

The accompanying drawings, which are incorporated into and form part of this disclosure, illustrate embodiments of the invention and together with the description, serve to explain the principles of the invention.

DETAILED DESCRIPTION OF THE INVENTION

The present invention provides a composition comprising a fluorescent sensor molecule'that can undergo intramolecular electron transfer which in turn modulates the fluorescence as a function of the concentration of an analyte such as glucose, galactose, or fructose. Using the present invention, fluorescent compounds can be designed that have desired fluorescent properties, such as selected absorption and emission wavelengths, high quantum yields, and longer fluorescence lifetimes. For example, compounds have been created with emission wavelengths greater than about 450 nm, and thus can be used to sense glucose in media with high opacities in visible blue or ultraviolet light, such as skin. In addition, compounds have been created with excitation wavelengths greater than about 400 nm, and thus have the benefit of being excited at wavelengths above ultraviolet. The compositions can be immobilized in a glucose permeable biocompatible polymer matrix to form a sensor that is implantable a few millimeters below the skin surface. The generalized compound comprises a substrate recognition component (a phenylboronic acid), a fluorescence switch component that acts as an electron donor (typically an amine), and a fluorophore that acts as an electron acceptor.

With the compounds described herein, in the absence of glucose, fluorescence quenching of the excited state fluorophore by the fluorescence switch component leads to a reduced background fluorescence level. In the presence of an analyte such as glucose, the glucose-recognition component reversibly forms a glucose boronate ester, resulting in a more electron deficient boron atom that ultimately interacts with or coordinates to the fluorescence switch. The complexation of glucose by the boronate inhibits the transfer of lone-pair electrons to the excited fluorophore, leading to an increase in fluorescence emission intensity and fluorescent lifetime, either of which can be accurately correlated to the ambient glucose concentration.

The fluorescent compound can be immobilized in a glucose permeable biocompatible polymer matrix to form an implantable sensor. Because of its long wavelength operating range, the sensor can be interrogated by applying excitation light through the skin and monitoring the intensity or lifetime of the emitted fluorescence externally. The measurement of emitted light thus allows quantification of glucose concentration.

Figure 1:
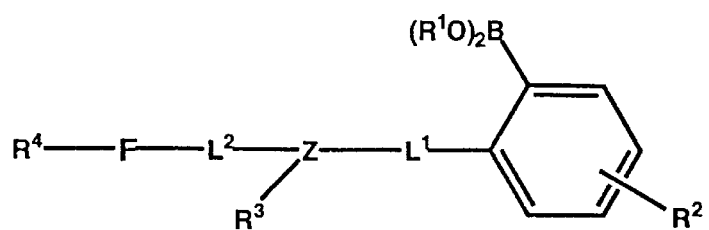
FIG. 1 shows the generalized formula of the fluorescent compound of the present invention.

The generalized sensor compound is shown in FIG. 1 and comprises three components: a fluorophore (F), a substrate-recognition site, and a fluorescence switch. The substrate recognition site is provided by a phenylboronic acid—$(C_6H_5)B(OR^1)_2$, where $R^1$ is hydrogen or lower aliphatic and aromatic functional groups. Preferably $R^1$ is hydrogen. The phenylboronic acid is bonded through optional linkage $L^1$ to the fluorescence switch Z, which is typically nitrogen (amine), but could be another electron donor heteroatom such as sulfur, phosphorus, or oxygen. The switch Z is bonded through a second optional linkage $L^2$ to the fluorophore F. The linkages $L^1$ and $L^2$ are 0–4 contiguous atoms selected from carbon, oxygen, nitrogen, sulfur and phosphorus. Optional groups $R^2$, $R^3$, and $R^4$ are attached respectively to the phenyl group, the switch Z, and the fluorophore F. Groups $R^2$, $R^3$, and $R^4$ may be functional groups that can form covalent linkages to a polymer matrix. Alternatively, $R^2$, $R^3$, and $R^4$ may be hydrogen or a lower aliphatic or aromatic functional group.

The present invention provides a reliable model for fluorescent sensor molecule development, which represents a tremendous advantage in the effort to create, for the first time, new glucose sensor molecules that have desired fluorescent properties, for example, to operate at more favorable wavelengths. This model allows a systematic build-up of a new molecule in small, relatively simple steps, rather than proceeding directly from a paper design of the molecule to a lengthy campaign to synthesize a single compound that may or may not prove viable. The likely multiple repetitions of the process required to eventually produce a satisfactory glucose sensor molecule are prohibitively time-consuming.

Using the disclosure provided herein, a modular approach to the construction of new fluorescent compounds is possible. With this new approach, a functioning glucose sensor molecule is created comprising the three functional components: a glucose-recognition component, a fluorescence on/off switch mediated by a glucose recognition event, and a fluorophore. The selection of fluorophore can be used to affect a number of molecular properties: excitation and absorption wavelength, quantum yield, fluorescence lifetime, photostability, chemical stability, solubility, temperature sensitivity, or pH sensitivity.

In order to design new molecular transducers, it is important to understand the mechanism by which signaling occurs. In the case of the compound shown in FIG. 1, fluorescence switching occurs by photoinduced electron transfer (PET), a common mechanism for such chemical transduction (see e.g. Serroni et al., *Chem-Eur J* 1999, 5, 3523–3527; Grigg et al., *J Chem S Ch* 1994, 185–187; Gust et al., *Account Chem Res* 1993, 26, 198–205; Kavarnos, G. J. In *Fundamentals of photoinduced electron transfer*; VCH Publishers: New York, N.Y., 1993; p Chapter 1; Wasielewski, M. R. *Chem Rev* 1992, 92, 435–461 and Balzani et al., In *Supramolecular photochemistry*; Ellis Horwood: New York, 1991; p Chapter 5.)

Figure 16:
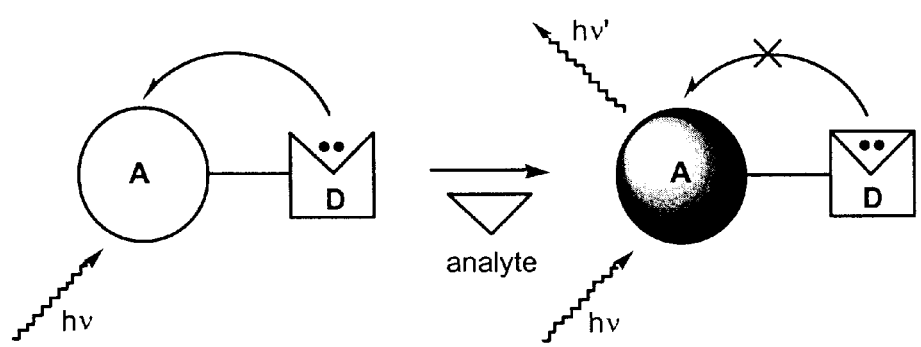
FIG. 16 shows a schematic drawing of PET sensors: a) in the absence of analyte, the electron donor (D) quenches the fluorescence of the electron acceptor/fluorophore (A); b) in the presence of analyte, electron transfer does not occur and A fluoresces.

A schematic of a typical PET sensor is shown in FIG. 16. As shown in FIG. 16, an electron donor (D), such as an amine, quenches the fluorescence of an electron acceptor (A) in absence of an analyte. When the analyte is present, the oxidation potential of D is lowered and electron transfer does not occur, giving an increase in fluorescence. Other systems are known to operate by PET, such as the ruthenium and rhenium bipyridine complexes reported by Meyer (Meyer, T. J. *Account Chem Res* 1989, 22, 163–170) and Lakowicz (Murtaza et al., *Anal Biochem* 1997, 247, 216–222) the naphthalimide and perylene systems reported by de Silva (Daffy et al., *Chem-Eur J* 1998, 4, 1810–1815 de Silva et al., *Chem Rev* 1997, 97, 1515–1566), and a variety of molecular sensors from Beer's group (Beer, P. D. *Account Chem Res* 1998, 31, 71–80). In these systems, the most common recognition elements are pendant amines, calixarenes, or crown ethers used for measuring pH or alkali metal concentration. Such systems are limited to the relatively few types of recognition elements available. The Examples include descriptions of the synthesis and fluorescence studies of new boronic acid derivatives of rhenium and ruthenium bipyridine complexes. Previously Yam has reported a rhenium bipyridyl complex for the transduction of saccharides by absorbance (see e.g. Yam et al., *Chem Commun* 1998, 109–110 and Mizuno et al., *J Chem Soc Perkin Trans* 1 2000, 407–413), and Shinkai has previously synthesized other types of organic and inorganic bipyridyl boronic acids (see e.g. Mizuno et al., *J Chem Soc Perkin Trans* 2 1998, 2281–2288).

Achieving successful interplay of the components of these sensors, resulting in optochemical glucose sensitivity, requires a precise matching of their electrochemical properties. Given a functioning glucose-sensor molecule, shifting the wavelength of operation (or lengthening fluorescence lifetime) cannot be accomplished by simply substituting the original fluorophore with another fluorophore of the desired wavelength (or lifetime). Rather, a fluorophore and a switch with compatible reduction and oxidation potentials and fluorophore photoexcitation energy must be selected. Similarly, modifications of the molecule, to accommodate immobilization of the molecule in a biocompatible substrate for example (suitable for surgical implantation), could alter the oxidation potential of the 'switch' component, thereby upsetting the electrochemical balance required for operation.

The search for new fluorescent glucose transducers based on photoelectron transfer (PET) requires, among other things, an understanding of the electrochemistry of any potential donor-acceptor pair. The free energy of PET ($\Delta G_{e1}$) can be calculated using the Rehm-Weller equation shown below:

$$\Delta G_{e1}(\text{kcal mol}^{-1}) = 23.06[E^0(D^+/D) - E^0(A/A^-)] - w_p - w_r - \Delta G_{00}$$

where $E^0(D^+/D)$ is the oxidation potential of the donor, $E^0(A/A^-)$ is the reduction potential of the acceptor, and $\Delta G_{00}$ is the free energy corresponding to the equilibrium energy $E_{00}$ (see e.g. Kavarnos, G. J. In *Fundamentals of photoinduced electron transfer*; VCH Publishers: New York, N.Y., 1993; p Chapter 1 and Rehm and Weller, Isr. J. Chem. 1970, 8, 259). The quantities $w_p$ and $w_r$ are Coulombic terms for the products and reactants, and are found to be small in polar solvents. To simplify predictions, we assume $w_p$ and $w_r$ to be zero, and estimate $E_{00}$ as the energy corresponding to $[\lambda_{max}(\text{ex}) + \lambda_{max}(\text{em})]/2$ for each fluorophore. While accurate $E_{00}$ values can also be found for example, in the literature for anthracene, $[\text{Ru}(\text{bipy})_3]^{2+}$, and a number of other compounds, we find this method of calculation useful for estimating equilibrium energies for new compounds that have not been previously reported.

Consequently, to create a functioning sensor molecule using the present invention, the thermodynamic requirement of the system that must be met is adherence to a simplified version of the Rehm-Weller equation as follows:

$$\Delta G_{PET} = 23.06[E^0(Z^{oxidation}) - E^0(F^{reduction})] - \Delta E_{00}],$$

where $\Delta G_{PET}$ is the standard free-energy change for electron transfer, $E^0(Z^{oxidation})$ is the oxidation potential of the switch (typically an amine), $E^0(F^{reduction})$ is the reduction potential of the fluorophore, and $\Delta E_{00}$ is the energy of the excited state fluorophore. To design a compound with the desired fluorescent characteristics entails selecting a fluorophore F with the desired properties and simultaneously selecting a switch Z with an oxidation potential that results in a $\Delta G_{PET}$ that is less than about 3.0 kcal mol$^{-1}$. The electrochemical potentials can be measured using the individual molecular groups before assembling the complete molecule.

The invention typically entails selecting F and Z to satisfy the Rehm-Weller equation disclosed herein such that $\Delta G$, the free energy for electron transfer is negative or at least only slightly positive. In particular, as shown by the representative molecules provided in the Examples below, the PET mechanism can be active even with slightly positive $\Delta G$ values due, for example, to slight measurement variability and other minor effects. Therefore, as a practical matter, with the fluorescent compounds described herein, the $\Delta G$ should be less than about 3.0 kcal mol$^{-1}$. Consequently, in preferred embodiments of the fluorescent compounds described herein, F and Z are selected to satisfy the equation such the $\Delta G$ is less than about 3.0 kcal mol$^{-1}$. In a more preferred embodiment, F and Z are selected to satisfy the equation such the $\Delta G$ is less than about 1.5 kcal mol$^{-1}$. In a highly preferred embodiment, F and Z are selected to satisfy the equation such that the $\Delta G$ is a negative value.

Applicants' teachings of functioning sensor molecules having a specified general molecular formula as shown in FIG. 1 wherein F and Z are selected to satisfy the energetic requirements of the simplified Rehm-Weller equation described herein allows the skilled artisan to generate a variety of novel molecules having exceptional activities including excitation wavelengths greater than about 400 nm and emission wavelengths greater than 450 nm. Functioning sensor molecules of this specific formula which have excitation wavelengths greater than about 400 nm are unexpected in view of the body of literature in this field which describes typical molecules as having excitation wavelengths that are significantly less than about 400 nm (see e.g. U.S. Pat. No. 5,763,238 to James et al.; U.S. Pat. No. 5,137,833 to Russell; James et al. "Novel Photoinduced Electron-transfer sensor for Saccharides Based on the Interaction of Boronic Acid and Amine", J. Chem. Soc. Chem. Comm., 477–478 (1994) and Sandanayake et al., "Molecular Fluorescence Sensor for Saccharides Based on Amino Coumarin", Chemistry Letters 139–140 (1995)). In addition, the functioning sensor molecules of this specific formula which have emission wavelengths greater than about 450 nm are unexpected in view of the body of literature in this field which teaches that the vast majority of these molecules have emission wavelengths that are significantly less than about 450 nm (see e.g. U.S. Pat. No. 5,763,238 to James et al.; U.S. Pat. No. 6,002,954 to Van Antwerp et al. and James et al. "Novel Photoinduced Electron-transfer sensor for Saccharides Based on the Interaction of Boronic Acid and Amine", J. Chem. Soc. Chem. Comm., 477–478 (1994)).

As illustrated by the representative molecules disclosed herein, by employing a defined molecular formula as shown in FIG. 1 where two variables F and Z are selected to satisfy the energetic requirements of the simplified Rehm-Weller equation one can determine which species among the multitude of species covered by the formula have thermodynamic characteristics which allow them to function as analyte sensors. Surprisingly, it was found that measurements made on the individual components of the boronate glucose sensing molecule having the formula shown in FIG. 1 afford an accurate prediction of the PET behavior of the final assembled molecule. Consequently, the Rehm-Weller equation disclosed herein can be employed to generate saccharide binding fluorescent compounds having tailored fluorescent activities such as higher excitation and emission wavelengths.

By relying on a defined molecular formula as shown in FIG. 1 where two variables F and Z are selected to satisfy the energetic requirements of the simplified Rehm-Weller equation, one can identify functioning boronate based saccharide sensing molecules without having to resort to the quantity of experimentation typically needed to identify such compounds. Moreover, as is known in the art, computer programs which perform equations with specified parameters can be employed to facilitate the identification of compounds having desired characteristics including specified thermodynamic properties (see e.g. McMartin et al., J. Comput. Aided Mol. Des. 1997, 11(4): 333–344; Lesying et al., Pharmacol. Ther. 1993, 60(2): 149–167, and Ritter J. Chem. Inf. Comput. Sci. 1991, 31(3): 400–408). In this context, one can employ such tools to evaluate compounds having the specific formula shown in FIG. 1 where F and Z are selected to satisfy the energetic requirements of the simplified Rehm-Weller equation. Moreover, as illustrated by the exemplary molecules identified and synthesized herein, this disclosure allows one to generate a variety of working examples which incorporate structurally dissimilar signal molecules including transition metal complex, conjugated organic heterocyclic ring system and naphthalimide fluorophores.

Sensor molecules having a specific molecular formula as shown in FIG. 1 where F and Z are selected to satisfy the energetic requirements of the simplified Rehm-Weller equation and where the excitation wavelength for F is greater than about 400 nm have a number of advantages over similar previously described molecules. For example, such molecules have the advantage of being excited at a wavelength outside of the ultraviolet spectra, and therefore are particularly suited for use in, for example, subdermally implanted optical glucose monitoring systems (See e.g. U.S. Pat. No. 6,011,984). In particular, ultraviolet light, which has a spectrum that extends up to, but not beyond 400 nm, is known to be able to induce cumulative damage to human skin (see e.g. Lavker et al., J. Invest. Dermatol., 108(1): 17–21 (1997) and Gasparro Environ. Health Perspect, 108 Sppl. 1: 71–78 (2000)). Consequently sensors designed to function with fluorophores having excitation wavelengths outside of this range can avoid potential problems associated with the use of fluorophores having excitation wavelengths which fall within a range that, in certain contexts, has been shown to induce cumulative damage to human skin. Moreover, because the matching of the peak excitation wavelength with an existing light source (such as an LED or diode laser) facilitates the generation and use of embodiments of the invention including their use in transdermally implanted glucose monitors, excitation wavelengths for F greater than about 400 nm have this additional advantage over similar previously described molecules.

Sensor molecules having a specific molecular formula as shown in FIG. 1 where F and Z are selected to satisfy the energetic requirements of the simplified Rehm-Weller equation and where the emission wavelength for F is greater than about 450 nm have a number of advantages over similar previously described molecules, particularly in their ability to transmit a signal through a tissue such as skin. Specifically, the transmission through a few millimeters of skin increases logarithmically with wavelength—from 0.1% at 400 nm to almost 100% at 850 nm (see e.g. Optical-Thermal Response of Laser-Irradiated Tissue (A. J. Welch and M. J. C. van Gemert eds., Plenum Press) (1995); Francis A. Duck, Physical Properties of Tissue (Academic Press) (1990) and Abraham Katzir, Lasers and Optical fibers in medicine (Academic Press) (1993). Thus, the longer the wavelength, the greater the transmission through skin. Because of the significant increase in optical skin transmission at longer wavelengths, a practical glucose sensor using the fluorescent molecules described herein can operate more efficiently, more accurately, and with a greater signal-to-noise ratio.

In typical embodiments of the present invention, the fluorophore (F) is a dye that has an excitation wavelength greater than 400 nm and an emission wavelength greater than 450 nm. Illustrative molecules provided herein fall into a variety of general categories including transition metal-ligand complexes, conjugated organic heterocyclic ring system compounds that are thiazines, oxazines, oxazine-ones, or oxazones, as well as anthracene complexes.

Figure 2:
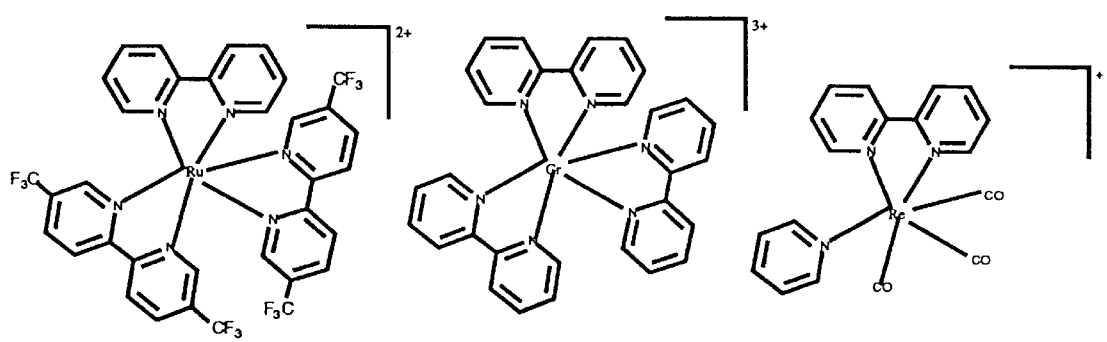
FIG. 2 shows examples of transition metal-ligand fluorophores according to the present invention.
Figure 3:
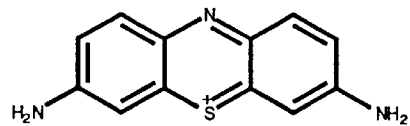
FIG. 3 shows an example of a thiazine fluorophore.
Figure 4:
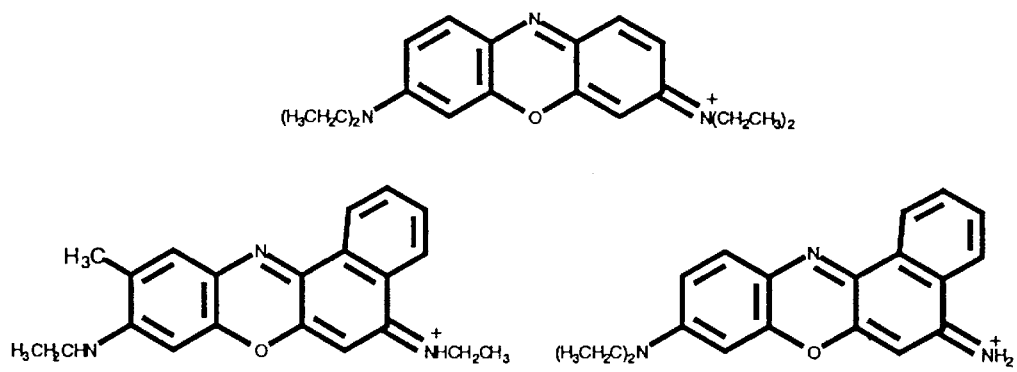
FIG. 4 shows examples of oxazine fluorophores.
Figure 5:
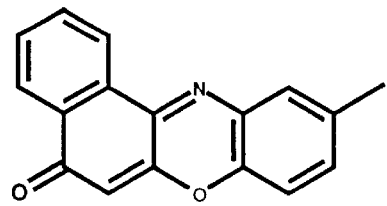
FIG. 5 shows examples of oxazine-one and oxazone fluorophores.

Specific examples of transition metal-ligand fluorophores are discussed in Example 1 and shown in FIG. 2 and include ruthenium bistrifluoromethylbipyridine, chromium bipyridine, and rhenium tricarbonyl bipyridine. As long as the thermodynamic requirement (Rehm-Weller equation) of the system is met as described above, other metals are possible, indeed any transition metal whose reduction/oxidation properties could be appropriately modified. Transition metals are those elements from Groups IIIA–IB in the periodic table, e.g., Co, Cr, Cu, Mo, Rh, Ru, W, Re, Os, Ir, and Pt. Specific examples of conjugated organic heterocyclic ring system fluorophores suitable for the present invention are discussed in Example 2 and shown in FIGS. 3–5. An example of a thiazine fluorophore is a thionine complex, as shown in FIG. 3, but would also include substituted systems like 1,9-dimethyl-methylene blue. The oxazine fluorophores include oxazine 1, oxazine 170, or Nile Blue complex, as shown in FIG. 4. An oxazine-one and an oxazone fluorophore are shown in FIG. 5. Specific examples of anthracene fluorophores suitable for the present invention are discussed in Example 3 and shown in FIGS. 25–29.

In one embodiment of the invention, the fluorophore was selected to lengthen the fluorescence lifetime of the sensor molecule. Specifically, the ruthenium complex, Ru(N-methyl benzyl boronate), for example, has a lifetime of 970 nanoseconds as contrasted with the COB (or anthracene-boronate) system with lifetimes of 10 ns or less. Thus, in addition to shifting the excitation/emission wavelengths, the substitution of this fluorophore has substantially altered the fluorescence lifetime of the sensor molecule.

The compounds of the present invention may be used in solution in bioassay studies to detect concentrations of saccharides or sugars, such as glucose. In another embodiment of the invention, the compounds may be immobilized in a biocompatible polymer matrix used for medical implants. The compounds are bound covalently to the polymer using techniques described in U.S. Pat. No. 6,002,954 which is hereby incorporated by reference. Basically, these methods involve adding a suitable tether to the molecule such that the tether can be used to covalently attach the compound to the matrix. The attachment point can be through $R^2$ or $R^3$ (see FIG. 1) or alternatively through the fluorophore itself via $R^4$. As an example, $R^2$ could be a 5-hydroxypentyl tether or linker arm that could react with an isocyanate group to form an end capped urethane/compound on a polymeric matrix. The tether itself could be further modified (e.g., by reaction with methacrolyl chloride to form a methacrylate ester) to present a linker that is suitable for incorporation in a free radical polymerized system such as an acrylic based hydrogel.

A number of sensors which employ glucose sensing molecules are known in the art and can be adapted for use with the compounds described herein. For example U.S. Pat. No. 5,628,310 to Rao et al., which is incorporated herein by reference, describes an apparatus and method to enable minimally invasive transdermal measurements of the fluorescence lifetime of an implanted element without reagent consumption and not requiring painful blood sampling. U.S. Pat. No. 5,476,094 to Allen et al., which is incorporated herein by reference, disclosed membranes which are useful in the fabrication of biosensors, e.g., a glucose sensor, intended for in vivo use. U.S. Pat. No. 6,040,194 to Chick et al., which is incorporated herein by reference, discloses in vivo methods and apparatuses for detecting an analyte such as glucose in an individual. U.S. Pat. No. 6,011,984 to Van Antwerp et al., which is incorporated herein by reference, discloses methods for the determination of the concentration of biological levels of polyhydroxylated compounds, particularly glucose. These methods utilize an amplification system that is an analyte transducer immobilized in a polymeric matrix, where the system is implantable and biocompatible. Upon interrogation by an optical system, the amplification system produces a signal capable of detection external to the skin of the patient. Quantitation of the analyte of interest is achieved by measurement of the emitted signal.

Figure 15:
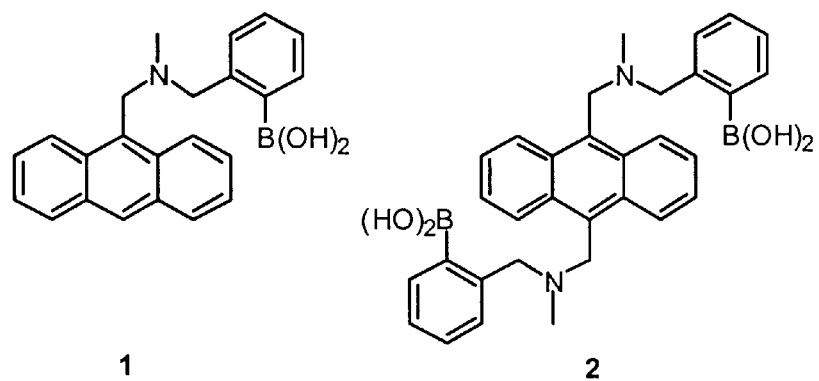
FIG. 15 shows exemplary saccharide sensing boronic acid derivatives of anthracene.

As discussed above, the invention provided herein is directed to novel analyte detection systems based on more robust, small molecule transducers. These molecules can be used in a number of contexts including subcutaneously implantable membranes that provide a fluorescent response to, for example, increasing glucose concentrations. Once implanted, the membranes can remain in place for long periods in time, with glucose measured through the skin by optical excitation and detection. A number of similar systems have been published previously, largely from Shinkai's group and primarily involving detection by colorimetry and circular dichroism spectroscopy (see erg. James et al., *Angew Chem Int Ed* 1996, 35, 1911–1922; Ward et al., *Chem Commun* 2000, 229–230 and Lewis et al. *Org Lett* 2000, 2, 589–592). A smaller set of compounds make use of fluorescence detection (see e.g. Kukrer et al., *Tetrahedron Lett* 1999, 40, 9125–9128; Kijima et al., *Chem Commun* 1999, 2011–2012 and Yoon et al., *J Amer Chem Soc* 1992, 114, 5874–5875), the most promising of these being Shinkai's boronic acid derivatives of anthracene, compounds 1 and 2 as shown in FIG. 15 (see e.g. James et al., *J Amer Chem Soc* 1995, 117, 8982–8987).

An illustrative compound known in the art (compound 1 in FIG. 15) as described by James shows an impressive 120% increase in fluorescence upon increasing glucose the glucose concentration of a solution from 0 to 300 mg/dL in 33% MeOH/phosphate buffered saline (PBS, pH 7.4). The main factors limiting the utility of this compound for use in a commercial sensor are its low solubility in water and the short wavelengths at which it undergoes excitation and emission. Water solubility is clearly needed for operation in vivo; fluorescence at long wavelengths is important due the greater transmission of visible light through the skin towards the red end of the spectrum. Similarly, a recent study by Akkaya and coworkers created a squaraine dye with an appended boronic acid group that shows modest increases in fluorescence with increasing glucose concentration (Kukrer, B.; Akkaya, E. U. *Tetrahedron Lett* 1999, 40, 9125–9128). As disclosed herein, we provide new molecules that overcome difficulties associated with known molecules such as excitation spectra below about 400 nm and emission spectra below about 450 nm.

Figure 14:
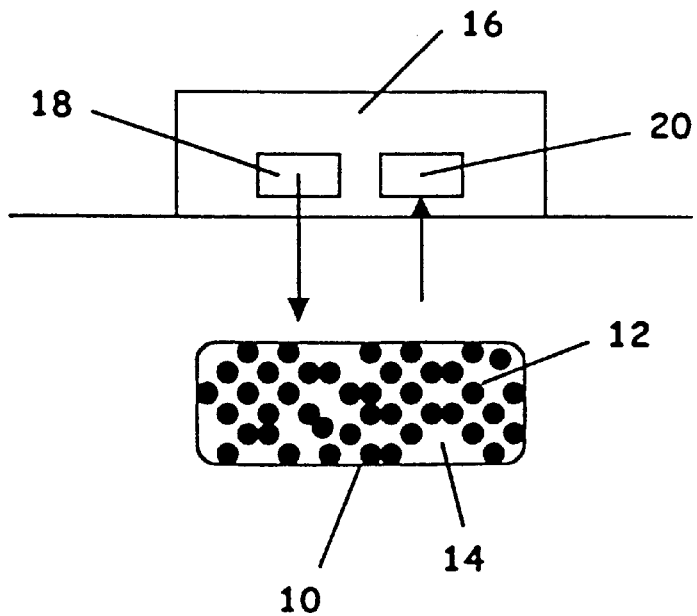
FIG. 14 shows an implantable glucose sensor system.

A typical implantable glucose sensor for use with the present invention is shown schematically in FIG. 14. The fluorescent compounds 12 are incorporated into the matrix 14 to form a small sensor 10, which is implanted about 1–3 mm below the skin surface. The sensor 10 is interrogated by an external instrument 16 that contains a light source 18 to excite the fluorescence and a detector 20 to measure the resultant emission. The detected optical signals are then converted into a glucose concentration. A calibration method is needed; either fluorescent lifetime measurement techniques are used or ratiometric methods using a second glucose insensitive fluorophore contained within the polymer.

As described below, certain specific embodiments of the invention consist of fluorescent saccharide binding compounds defined by a specified chemical identity (for example the general formula shown in FIG. 1), and wherein substituent molecules of these compounds are selected to have complimentary molecular properties which can be determined via simplified version of the Rehm-Weller equation and, additionally, have a specific desirable functional activity such as an excitation wavelength greater than 400 nm and/or an emission wavelength greater than 450 nm (e.g. the compound fluoresces at a wavelength greater than about 450 nm in the presence of an analyte such as glucose). Such embodiments are comparable to polypeptide chemicals of a specific formula (i.e. an amino acid sequence of a protein), selected to share a certain structural identity with a specified sequence (i.e. % identity) and which have a defined and measurable function (e.g. catalyze a reaction of A→B etc.). Functioning compounds defined by a specific chemical formula whose constituents are selected to meet thermodynamic requirements in order to obtain molecules having a certain activity can be, however, more easy to generate than functional polypeptides characterized as having a certain % of identity with a defined sequence because, unlike mere % identity, the simplified Rehm-Weller equation can be used to identify compounds likely to exhibit a specific desirable function before such compound is generated.

Although the sensor molecules for sugars like glucose are of primary interest for biomedical applications, the present sensor/transducer scheme is useful more generally for the measurement of any cis-diol. For example, the present sensor molecules have utility in the measurement of ethylene glycol contamination in boiler waters, where ethylene gycol contamination is an indication of heat exchanger tube degradation as well as other uses in similar contexts (see e.g. U.S. Pat. No. 5,958,192). These sensor molecules, can be of use in industrial fermentation processes (e.g. beer and wine), or in any number of process points in the production of high fructose corn syrup such as. enzyme reactors and the like (see e.g. U.S. Pat. No. 5,593,868; U.S. Pat. No. 4,025,389; Ko et al., Biotechnol. Bioeng. 57(4): 430–437 (1998) and Mou et al., Biotechnol. Bioeng. 18(10): 1371–1392 (1976)). Moreover, sensor molecules described herein exhibit characteristics which them particularly suited for uses such as the monitoring of industrial fermentation processes. In particular, the compounds described in the Examples below exhibit varying degrees of sensitivity to concentrations of analytes, properties which may be advantageous for use in the context of monitoring solutions of industrial fermentation processes where such solutions have analyte concentrations that exceed those observed, for example, in vivo. In addition, the compounds described in the Examples below function in a wide pH range and in the presence of high concentrations of alcohols such as methanol (see e.g. FIG. 29), a property which can be advantageous in the context of monitoring fermentation processes.

As described herein, synthesis schemes for generating molecules such as those having the specific formula shown in FIG. 1, have been known in the art for some time (see e.g. James et al., *J. Am. Chem. Soc.* 1995, 117, 8982 and Sandanayake et al., "Molecular Fluorescence Sensor for Saccharides Based on Amino Coumarin", Chemistry Letters 139–140 (1995); Czarnik Acc. Chem. Res. 27, 302–308 (1994); Mohler et al., J. Am. Chem. Soc. 115, 7037–7038 (1993) and Deetz & Smith Tetrahedron Letters 1998, 39, 6841–44.). Moreover, as shown in the Examples below, Applicants provide detailed descriptions for the synthesis of a variety of specific compounds of the invention (e.g. defined by a specific formula and wherein substituent molecules of these compounds are selected to have complimentary molecular properties which can be determined via simplified version of the Rehm-Weller equation) including those that utilize transition metal-ligand complexes, conjugated organic heterocyclic ring system compounds that are thiazines, oxazines, oxazine-ones, or oxazones and anthracene fluorophores. In addition, those skilled in the art will understand that the simplified version of the Rehm-Weller equation described herein can be employed to facilitate the actual synthesis of such modular compounds. In particular, in situations where the synthesis of a compound having a certain constituent group (e.g. methyl) may entail less cost or effort than is required synthesis of a compound having a similar constituent group (e.g. ethyl), the simplified version of the Rehm-Weller equation can be employed to confirm that a more cost effective or easily synthesized compound maintains the thermodynamic properties that allow it to function as an analyte sensor. Consequently, by using the disclosure provided herein, one can reduce the amount of effort normally employed in the generation of such compounds.

The disclosure provided herein teaches a number of embodiments of the invention. Typically, the invention consists of a fluorescent compound that emits a signal that can be correlated to an analyte (such as a saccharide) concentration and where the compound has the general specified formula shown in FIG. 1. In this formula, $R^1$ is typically selected from the group consisting of hydrogen and lower aliphatic and aromatic functional groups; $R^2$ and $R^4$ typically are hydrogen, optional lower aliphatic or aromatic functional groups or functional groups that can form covalent bonds to the polymer matrix; $L^1$ and $L^2$ typically are optional linking groups having from zero to four atoms selected from the group consisting of nitrogen, carbon, oxygen, sulfur, and phosphorus; Z is a heteroatom selected from the group consisting of nitrogen, sulfur, oxygen and phosphorus; $R^3$ typically is an optional group selected from the group consisting of hydrogen, lower aliphatic or aromatic functional groups; and groups that form covalent bonds to the polymer matrix; and F is a fluorophore with selected molecular properties. Typically, F and Z are selected to satisfy the following equation such that $\Delta G$, the free energy for electron transfer, is less than about 3.0 kcal $mol^{-1}$: $\Delta G = 23.06 \ [E^0(Z^{oxidation}) - E^0(F^{reduction})] - \Delta E_{00}$, wherein $E^0(Z^{oxidation})$ is the oxidation potential of Z, $E^0(F^{reduction})$ is the reduction potential of F, and $\Delta E_{00}$ is the energy of F in the excited state. In the preferred embodiments of this invention, the fluorescent compound emits a signal that is correlated with the concentration of glucose.

Examples of typical fluorophores (F) in the above formula include a variety of moieties or functional groups containing π-electron systems. Preferred fluorophores include transition metal-ligand complexes, oxazines, oxazine-ones, oxazones, thiazines, and naphtyl, anthryl, pyrenyl and phenanthryl compounds. The fluorophore-forming atomic or functional groups can be substituted ones as long as the substituent(s) do not alter the thermodynamic characteristics of the compounds in a way that adversely affect the fluorescence. For example, the substitution with sulfonic acid group(s) may occur, particularly when the compound is to be dissolved in an aqueous fluid for the detection of saccharides contained therein, as it imparts the compound with water-solubility. In one embodiment of the invention, a substituent R group such as $R^1$, $R^2$, or $R^3$ (combined with the nitrogen atom), denotes hydrogen, groups that form covalent bonds to the polymer matrix such as a 5-hydroxypentyl tether or linker arm that can react with an isocyanate group to form an end capped urethane/compound on a polymeric matrix, or are a lower aliphatic or aromatic functional group. In specific embodiments, R can be alkyl group having 1 to 6 carbon atoms, i.e. methyl, ethyl, propyl or butyl, or phenyl group. In addition, in such embodiments, the phenyl group composing the phenylboronic acid may be substituted with an appropriate substituent or substituents as long as the subsitutions discussed herein do not adversely affect the fluorescence. Examples of candidate substituents include methyl, ethyl, propyl, butyl, phenyl, methoxy, ethoxy, butoxy, phenoxy, pyridyl, furanyl, thiophene and pyridone groups.

In preferred embodiments of the invention, F typically emits at a wavelength greater than about 450 nm. In preferred embodiments of the invention, F emits at a wavelength greater than about 500 nm, a wavelength greater than about 550 nm or a wavelength greater than about 600 nm. In highly preferred embodiments, the excitation wavelength for F is greater than about 400 nm or greater than about 450 nm. In this context, those skilled in the art understand that the excitation and emission wavelengths of such molecules are found over in a focused spectrum of wavelengths and do not occur at a single absolute point. Consequently, with molecules that, for example, have an emission maximum centered near 450 nm, it is therefore accurate to describe such molecules as typically emitting at a wavelength greater than about 450 nm. In addition, with molecules that, for example, have an excitation maximum centered near 450 nm, it is therefore accurate to describe such molecules in such terms as having an excitation wavelength that is greater than about 400 nm. For a general description of the properties of fluorescent molecules and fluorescent techniques, see "Introduction to Fluorescence Techniques" from the Handbook of Fluorescent Probes and Research Chemicals, portions of which can be found online at http://www.probes.com (specifically at http://www.probes.com/handbook/sections/0069.html).

In specific embodiments of this invention Z is typically nitrogen. In more specific embodiments of this invention F is selected from the group consisting of transition metal-ligand complexes, oxazines, oxazine-ones, oxazones, thiazines and anthracenes. In even more specific embodiments of the invention, F comprises an oxazine-one boronate, an anthracene-boronate or a transition metal-ligand complex comprising a metal selected from the group consisting of ruthenium and chromium.

The detection with the fluorescent compound of the present invention can be performed by adding the compound to the sample and by a photoscopic method, determining the increased intensity of the fluorescence due to the binding of the compound with the saccharide. Alternatively, the detection with the fluorescent compound of the present invention may be conducted by a chromatographic method where the compound of the present invention is supported on a supporting material through which the saccharide-containing sample is passed for the detection based on the increased fluorescent intensity due to the complex of the compound and the saccharide. In this context, another typical embodiment of the invention is a sensor comprising a polymer matrix containing a fluorescent compound as discussed above. In such embodiments, the fluorescent compound is typically covalently bonded to a polymer matrix, and the matrix is biocompatible and implantable.

Other embodiments of the invention include a method for analyzing the concentration of an analyte in a sample by using a fluorescent compound as discussed above and introducing the fluorescent compound into a sample, measuring the fluorescence of the compound in the sample in the presence of the analyte and then determining the concentration of the analyte from the fluorescence measurement. In preferred embodiments of this method of the invention, the fluorescent compound is covalently bonded to a polymer matrix, wherein the matrix is biocompatible and implantable and the analyte comprises glucose. In a specific embodiment of this method of the invention, the measurement of fluorescence comprises measuring the intensity. In an alternative embodiment of this method of the invention, the measurement of fluorescence comprises measuring the lifetime.

As noted above, in typical embodiments of the invention, the fluorescent saccharide binding compounds disclosed herein are defined by a specific formula, substituent molecules of which have complimentary molecular properties that can be determined via simplified version of the Rehm-Weller equation. In particular, the invention provided compounds of the specific formula shown in FIG. 1, wherein F and Z are selected to satisfy the Rehm-Weller equation disclosed herein such that $\Delta G$, the free energy for electron transfer, is less than about 3.0 kcal mol$^{-1}$. In this context, constituents such as the fluorophore F can be selected to satisfy this equation by so assessing the thermodynamic properties of any one of the wide variety of fluorophores known in the art that are capable of being incorporated into this molecule, and in this way identify those with the appropriate characteristics. As noted above, various permutations of this selection process are contemplated including the use of computer programs to efficiently test a wide variety of candidate molecules. Alternatively, once a molecule that satisfies the Rehm-Weller equation disclosed herein such that $\Delta G$, the free energy for electron transfer, is a is less than about 3.0 kcal mol$^{-1}$ has been identified, one can use this information to select and test molecules having formulae reasonably expected to have thermodynamically analogous properties.

The foregoing description of preferred embodiments of the invention is presented for purposes of illustration and description and is not intended to be exhaustive or to limit the invention to the precise form disclosed. Many modifications and variations are possible in light of the above teaching. The embodiments were chosen and described to best explain the principles of the invention and its practical application to thereby enable others skilled in the art to best use the invention in various embodiments and with various modifications suited to the particular use contemplated.

The present invention is further detailed in the following Examples, which are offered by way of illustration and are not intended to limit the invention in any manner. All patent and literature references cited in the present specification are hereby incorporated by reference in their entirety.

EXAMPLES

Example 1

Transition Metal-ligand Fluorophores

Figure 6:
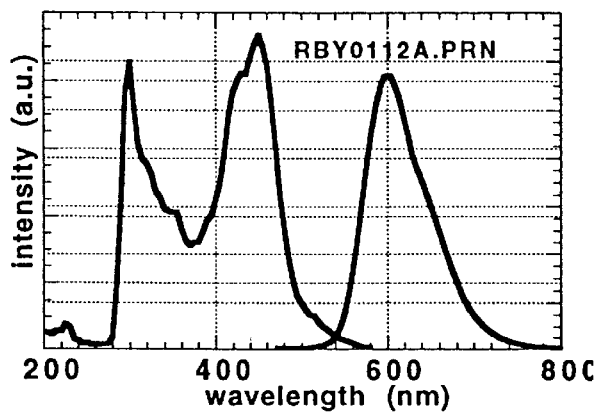
FIG. 6 shows the excitation and emission spectra of Ru(bistrifluoromethylbipyridine) in methanol/buffer.

To investigate transition metal-ligand complexes, a ruthenium ligand complex fluorophore was studied. FIG. 6 shows the excitation and emission spectra of Ru(bistrifluoromethylbipyridine) in buffer/methanol. The compound is excited at 460 nm, which is favorable for transdermal excitation, and emits well above 550 nm. Derivatives of this base fluorophore exhibit virtually the same excitation and emission spectra. From a device perspective, 460 nm excitation is easily accomplished with low-cost, commercially available ultra-bright LED light sources. In the example that follows, the excitation and emission wavelengths used were 460 and 560 nm, respectively, although operation at even higher wavelengths (red) is clearly possible.

Figure 7:
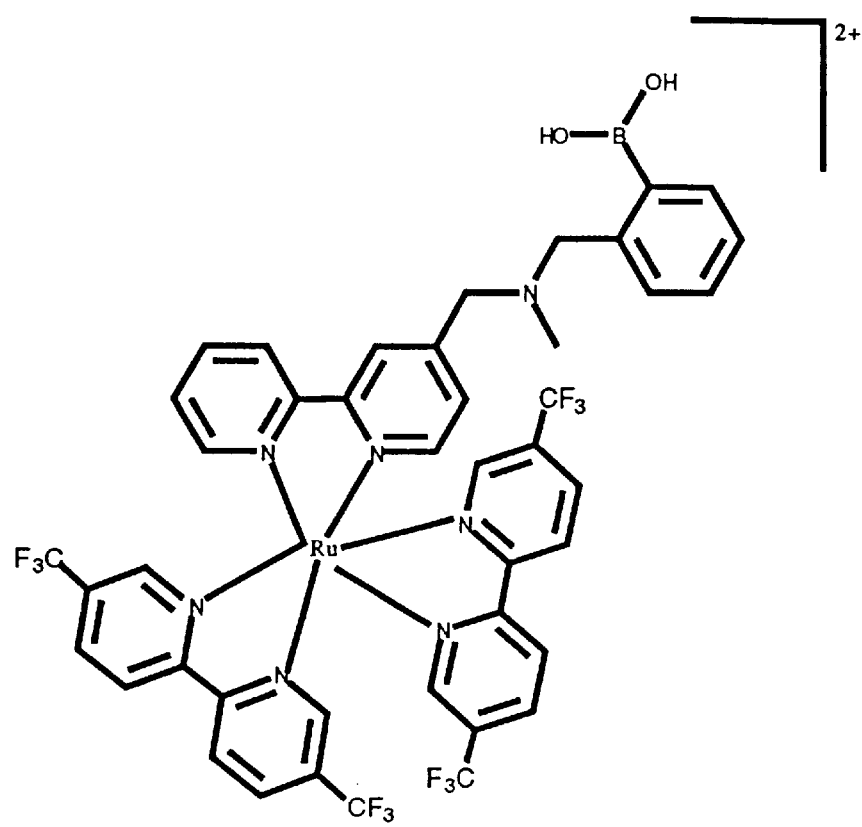
FIG. 7 shows Ru(N-methyl benzyl boronate).
Figure 8:
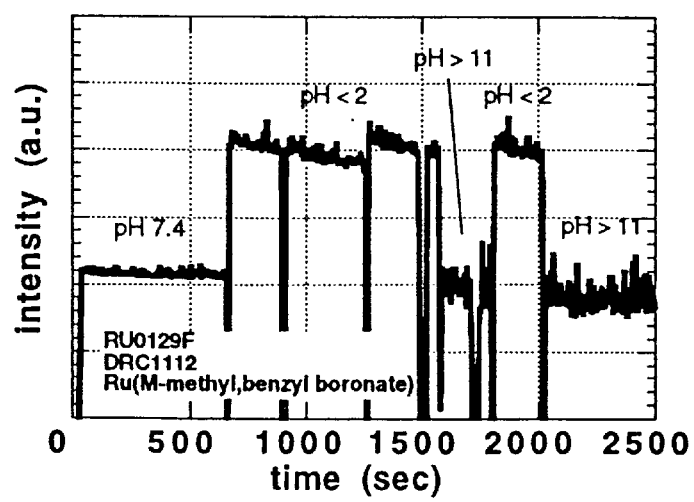
FIG. 8 shows a time history of Ru(N-methyl benzyl boronate) with additions of acid and base.

A glucose-sensing compound using the ruthenium fluorophore was synthesized: Ru(N-methyl benzyl boronate). The relevant values for the Ru(N-methyl benzyl boronate) system for the Rehm-Weller equation are: $\Delta G_{PET}$=$-7.4$ kcal/mole, $E^0(Z^{ox})$=0.95V, $E^0(F^{red})$=$-0.85$V, and $\Delta E_{00}$=48.9 kcal/mole. The compound is shown in FIG. 7. Samples of Ru(N-methyl benzyl boronate) were prepared at 10 $\mu$M concentration in distilled water. FIG. 8 shows a time history of this sample with additions of acid and base. The behavior of this compound under acidic and basic conditions is a good indicator of whether or not the final compound maintains PET functionality.

Following an initial period in which the baseline fluorescence is established, alternate additions of acid and base step the pH between values of 2 and 11. In response, the fluorescence intensity increases at the low pH, and decreases at the high pH. This is a nominally reproducible trend, at least to within the accuracy required in this set of screening tests. A trend in the data, namely the steady but slow decrease in the fluorescence intensity, is sometimes the signature of photo-bleaching, or it may indicate that the compound is unstable at extremes in pH.

For the glucose-sensor molecule Ru(N-methyl benzyl boronate) in solution, the ambient pH will determine the initial level of fluorescence in the absence of glucose. The lower this initial level is, the larger the achievable change of relative fluorescence. It appears that the ruthenium compounds are inherently capable of large changes in fluorescence because the pH 7 level of fluorescence is very close to that of the pH 11 value.

Figure 9:
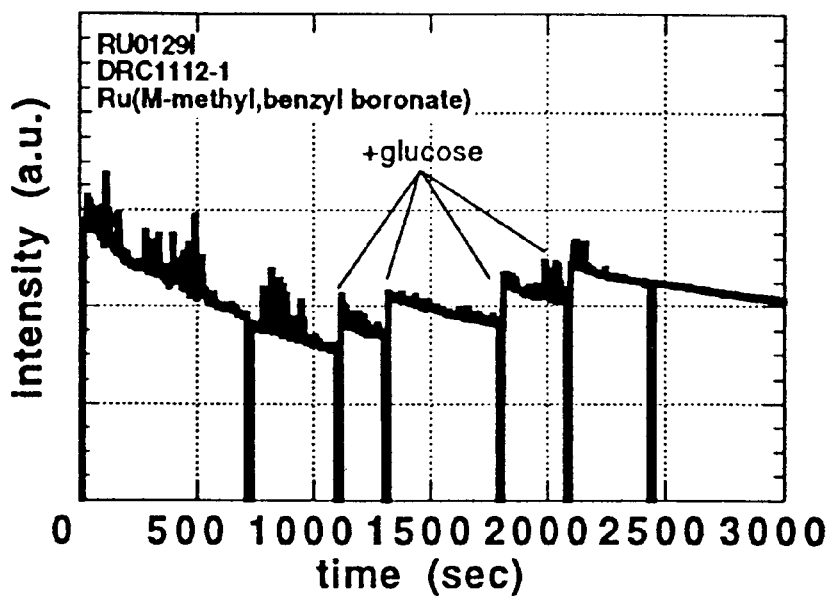
FIG. 9 shows a time history of Ru(N-methyl benzyl boronate) with additions of glucose.

The Ru(N-methyl benzyl boronate) compound was tested for glucose sensitivity. A sample was prepared at a concentration of 10 $\mu$M in distilled water. Multiple additions of glucose were made as shown in FIG. 9. Again, an intensity decay trend is superimposed on the data. Increases in the fluorescence corresponding to increases in the glucose concentration are clearly observed. The final glucose concentration is approximately 3000 mg/dL, clearly outside the clinical range, 50–500 mg/dL. Nevertheless, this increase gave rise to a fluorescence increase of approximately 50%. Although only a relatively small increase in fluorescence is expected for this compound over the clinical range of glucose concentrations, these results signify the first successful attempt to create a long-wavelength glucose-sensor molecule. Chemical modification of the molecule may permit one to maximize its response to changes in glucose concentration.

General Protocols

All reactions were performed under an atmosphere of $N_2$, followed by work-up in air. Protected boronate esters were stored under vacuum to prevent hydrolysis over long periods of time. Toluene and THF were distilled from sodium/benzophenone under $N_2$; dichloromethane and acetonitrile were distilled from calcium hydride under $N_2$. 4,4'-Dimethyl-2,2'-bipyridine (bpyMe) was purchased from Aldrich or GFS Chemicals. The compounds 4-(bromomethyl)-4'-methyl-2,2'-bipyridine (bpyCH$_2$Br), 2,2-dimethylpropane-1,3-diyl[o-(bromomethyl)phenyl]boronate (3), 4-(diethylaminomethyl)-4'-methyl-2,2'-bipyridine (bpyCH$_2$NEt$_2$), [(bpyCH$_2$NEt$_2$)Re(CO)$_3$(py)](OTf) (py=pyridine, OTf=trifluorosulfonyl), 5,5'-bis(trifluoromethyl)-2,2'-bipyridine (bpyF), and Ru(bipyF)$_2$Cl$_2$ were prepared by literature methods (see Hamachi et al., *Inorg Chem* 1998, 37, 4380–4388; Strouse et al., *Chem* 1995, 34, 473–487; Imperiali et al., *J Org Chem* 1993, 58, 1613–1616; Shen, Y. Ph. D., University of Wyoming, Laramie, Wyo., 1996 and Furue et al., *Inorg Chem* 1992, 31, 3792–3795).

Samples for FT IR spectroscopy were prepared as solutions in CHCl$_3$, and only the C=O stretches are reported. Unless otherwise stated, all NMR spectra were recorded at 500 MHz for $^1$H and 125 MHz for $^{13}$C at 20–25° C. using CDCl$_3$ as the solvent. Unless stated otherwise, mass spectra were obtained using electrospray ionization (50 V) with a 50/50 methanol/water solvent mixture with 1% acetic acid added. Cyclic voltammetry was conducted using a glassy carbon working electrode, platinum counter electrode, and Ag/AgCl reference electrode and carried out in a 0.1 M solution of NBu4ClO$_4$ in acetonitrile.

Fluorescence Measurements

Samples for fluorescence were prepared as 1.00 mM stock solutions in MeOH. A 30.0 $\mu$L aliquot of solution was then added to 3.000 mL of the appropriate solvent mixture (a combination of methanol and phosphate buffered saline—PBS) giving a final concentration of 10.0 $\mu$M for each complex. Changes in pH were carried out by the addition of small volumes of 1.0 M hydrochloric acid, 1.0 M sodium hydroxide, or glacial acetic acid. Glucose additions were performed by the addition of a concentrated solution of glucose in PBS to a stirred solution of fluorophore in a cuvette. Fluorescence measurements were made as a function of pH and glucose concentration by exciting the fluorophore at its peak excitation wavelength and measuring fluorescence intensity at the peak emission wavelength (for [(bpyX)Re(CO)$_3$(Py)](OTf) $\lambda_{ex}/\lambda_{em}$=361 nm/552 nm, for [(bpyX)Ru(bpyF)$_2$]Cl$_2$ $\lambda_{ex}/\lambda_{em}$=450 nm/635 nm). The protected boronate esters [(bpyNB)Re(CO)$_3$(Py)](OTf) and [(bpyNB)Ru(bpyF)$_2$]Cl$_2$ for our spectroscopic studies, rather than isolate the deprotected compounds, due to ease of synthesis. Control experiments were carried out by NMR and fluorescence spectroscopy to demonstrate that the presence of even small amounts of water in methanolic solution resulted in immediate and quantitative removal of the neopentyl glycol protecting group. This is in accordance with results by Shinkai indicating extremely weak binding constants for simple diols compared to saccharides for other boronate systems (see e.g. James et al., *J Amer Chem Soc* 1995, 117, 8982–8987), and NMR studies by Norrild in which trace amounts of water affect the binding mode of saccharides and boronates (Bielecki et al., *J Chem Soc Perkin Trans* 2 1999, 449–455).

4-(Methylaminomethyl)-4'-methylbipyridine (bpyCH$_2$NMeH). A stream of MeNH$_2$ gas was bubbled through a solution of bpyCH$_2$Br (1.52 g, 5.76 mmol) in 75 mL of THF at 0° C. for 15 min to give a cloudy colorless solution. The solution was allowed to warm to ambient temperature and stirring continued for 16 hours. The solvent was removed to give an oily white solid. A pale yellow solution was extracted from a white powder with diethyl ether and the solvent removed under vacuum to give bpyCH$_2$NMeH (1.20 g, 98%) as a pale yellow liquid. $^1$H NMR: δ 8.62 (d, 1H, J=4.9 Hz), 8.53 (d, 1H, J=4.9 Hz), 8.33 (s, 1H), 8.23 (s, 1H), 7.31 (d, 1H, J=4.3 Hz), 7.13 (d, 1H, J=4.4 Hz), 3.86 (s, 2H), 2.48 (s, 3H), 2.44 (s, 3H), 1.44 (br s, 1H). $^{13}$C{$^1$H} NMR: δ 156.3, 155.9, 150.3, 149.2, 148.9, 148.1, 124.7, 122.9, 122.0, 120.4, 54.9, 36.1, 21.2. GC/EIMS: m/z 212 (M–H)$^+$, 184 (bpyMe)$^+$.

4-(N-Benzylmethylaminomethyl)-4'-methylbipyridine (bpyN). A solution of HNMe(CH$_2$Ph) (0.680 mL, 5.27 mmol) in 5 mL of CH$_2$Cl$_2$ was added dropwise to a solution of bpyCH$_2$Br (0.693 g, 2.63 mmol) in 30 mL of CH$_2$Cl$_2$ over a few min to gradually give a golden solution. Stirring was continued for 2 hours and the solvent removed under vacuum. The crude was dissolved in 40 mL of CHCl$_3$ and 30 mL of H$_2$O added. A saturated solution of sodium carbonate was added to adjust the pH to 8. The layers were separated, followed by washing of the organic layer with 2×30 mL H$_2$O. with The solvent was removed to give an oily white solid. A pale yellow solution was extracted from a white powder with diethyl ether and the solvent removed under vacuum to give bpyN (1.20 g, 98%) as a pale yellow liquid. 1H NMR: δ 8.62 (d, 1H, J=4.9 Hz), 8.53 (d, 1H, J=4.9 Hz), 8.33 (s, 1H), 8.23 (s, 1H), 7.31 (d, 1H, J=4.3 Hz), 7.13 (d, 1H, J=4.4 Hz), 3.86 (s, 2H), 2.48 (s, 3H), 2.44 (s, 3H), 1.44

(br s, 1H). $^{13}C\{^1H\}$ NMR: δ 156.9, 156.6, 150.4, 149.8, 149.6, 148.7, 139.4, 129.5, 128.9, 127.7, 125.3, 124.4, 122.7, 121.9, 62.8, 61.4, 43.0, 21.8. GC/EIMS: m/z 302 (M−H)$^+$, 184 (M−NMeCH$_2$Ph)$^+$.

2,-Dimethylpropane-1,3-diyl[o-(methylaminomethyl) phenyl]-boronate (4). A stream of MeNH$_2$ gas was bubbled through a solution 3 (7.02 g, 24.8 mmol) in 150 mL of CH$_3$CN at 0° C. for 20 min to give a yellow solution. Stirring was continued for 3 hours and the reaction allowed to warm to room temperature. The solvent was removed under vacuum to give a yellow powder. A yellow solution was extracted from a white powder with chloroform and the solvent removed under vacuum to give 4 (5.48 g, 95%) as a pale yellow powder. $^1H$ NMR: δ 7.54 (d, 2H, J=6.8 Hz), 7.19 (m, 2H), 6.98 (d, 2H, J=7.2 Hz), 3.82 (s, 2H), 3.53 (s, 4H), 1.01 (s, 6H). $^{13}C\{^1H\}$ NMR: 6 140.8, 130.0, 127.7, 127.3, 123.0, 72.5, 55.8, 35.2, 32.4, 22.5. ESIMS: m/z 234.1 (M+H)$^+$.

4-{N-[o-(5,5-dimethylborinan-2-yl)benzyl]-N-methylamino]methyl}-4'-methylbipyridine (bpyNB). Method A. A solution 3 (1.60 g, 5.64 mmol) in 60 mL of THF was added dropwise over 1 hour to a solution of bpyCH$_2$NMeH (1.204 g, 5.65 mmol) and NEt$_3$ (0.787 mL, 5.65 mmol) in 60 mL of THF to give a cloudy white mixture by the end of addition. Stirring was continued for 1 hour, then the solvent removed under vacuum. The crude solid was extracted with diethyl ether and the solvent removed to give pure bpyNB (1.91 g, 82%) as an cream colored to white powder. Method B. A mixture of bpyCH$_2$Br (0.525 g, 2.00 mmol) and 4 (0.927 g, 3.99 mmol) was dissolved in 40 mL of THF to immediately give a cloudy white mixture. The reaction was stirred for 1 hour, then the solvent removed under vacuum. The crude solid was extracted with diethyl ether and the solvent removed under vacuum to give pure bpyNB (0.424 g, 51%) as a pale yellow solid. $^1H$ NMR: δ 8.64 (d, 1H, J=5.1 Hz), 8.54 (d, 1H, J=4.9 Hz), 8.32 (s, 1H), 8.24 (s, 1H), 7.64 (d, 1H, J=7.0 Hz), 7.34–7.23 (m, 4H), 7.14 (d, 1H, J'2 4.3 Hz), 3.77 (s, 4H), 2.44 (s, 3H), 2.29 (s, 3H), 1.05 (s, 6H). $^{13}C\{^1H\}$ NMR: d 156.5, 156.0, 149. 5, 149.3, 149.2, 148.3, 133.2, 129.0, 127.7, 125.0, 124.9, 123.9, 122.4, 122.2, 121.5, 72.5, 61.3, 59.9, 42.1, 32.1, 22.2, 21.4. ESIMS: m/z 348.0 (unprotected M+H)$^+$.

(bpyMe)Re(CO)$_3$Cl. The preparations of (bpyMe)Re(CO)$_3$Cl, (bpyN)Re(CO)$_3$Cl, and (bpyNB)Re(CO)$_3$Cl are analogous to that of (bpyCH$_2$NEt$_2$)Re(CO)$_3$Cl. A mixture of Re(CO)$_5$Cl (774 mg, 2.14 mmol) and bpyMe (394 mg, 2.14 mmol) in 40 mL of CH$_2$Cl$_2$ and 120 mL of toluene was heated at reflux for 2 hours to give a bright yellow-orange solution. The solvent was removed under vacuum and the crude material recrystallized from CH$_2$Cl$_2$/hexanes to give (bpyMe)Re(CO)$_3$Cl as a pure yellow powder (1.00 g, 95%). $^1H$ NMR 6 8.89 (d, 2H, J=5.6 Hz), 7.98 (s, 2H), 7.34 (d, 2H, J=5.6 Hz), 2.58 (s, 6H). $^{13}C\{^1H\}$ NMR: δ 197.5, 155.6, 152.8, 151.4, 128.1, 123.9, 21.9. ESIMS: m/z 454.8 (M−Cl)$^+$. IR: $v_{CO}$=2022, 1917, 1895 cm$^{-1}$.

(bpyN)Re(CO)$_3$Cl. The reaction of Re(CO)$_5$Cl (299 mg, 0.827 mmol) and bpyN (251 mg, 0.827 mmol) gave (bpyN)Re(CO)$_3$Cl as a yellow powder (486 mg, 96%). $^1H$ NMR: δ 8.91 (d, 1H, J=5.6 Hz), 8.86 (d, 1H, J=5.6 Hz), 8.19 (s, 1H), 7.98 (s, 1H), 7.50 (d, 1H, J=5.6 Hz), 7.38 (m, 4H), 7.31 (m, 2H), 3.66 (s, 4H), 2.57 (s, 3H), 2.32 (s, 3H). $^{13}C\{^1H\}$ NMR: δ 197.5, 190.0, 155.8, 155.6, 153.7, 152.9, 152.7, 151.5, 138.2, 129.1, 128.8, 128.1, 127.8, 126.8, 124.1, 122.6, 62.5, 60.0, 43.1, 21.9. ESIMS: m/z 574.0 (M)$^+$. IR: $v_{CO}$=2022, 1917, 1895 cm$^{-1}$.

(bpyNB)Re(CO)$_3$Cl. The reaction of Re(CO)$_5$Cl (310 mg, 0.857 mmol) and 6 (357 mg, 0.860 mmol) gave 7 as a yellow powder (560 mg, quantitative yield). $^1H$ NMR: δ 8.84 (d, 1H, J=5.4 Hz), 8.83 (d, 1H, J=5.4 Hz), 8.10 (s, 1H), 8.02 (s, 1H), 7.70 (d, 1H, J=7.0 Hz), 7.28 (m, 5H), 3.87 (d, 1H, J=12.2 Hz), 3.77 (d, 1H, 12.2 Hz), 3.72 (s, 4H), 3.46 (s, 2H), 2.58 (s, 3H), 2.35 (s, 3H), 1.00 (s, 6H). $^{13}C\{^1H\}$ NMR: δ 197.5, 190.1, 155.7, 155.6, 153.4, 152.6, 152.5, 151.3, 144.1, 134.2, 129.7, 129.2, 127.9, 127.2, 127.0, 124.4, 124.0, 72.5, 62.5, 59.2, 44.0, 32.0, 22.0, 21.7. ESIMS: m/z 654.0 (unprotected M+H)$^+$, 618.0 (unprotected M−Cl)$^+$. IR: $v_{CO}$=2021, 1917, 1895 cm$^{-1}$.

(bpyMe)Re(CO)$_3$(py)](OTf). The preparations of [(bpyMe)Re(CO)$_3$(Py)](OTf), [(bpyN)Re(CO)$_3$(Py)](OTf), and [(bpyNB)Re(CO)$_3$(py)](OTf) are analogous to that of [(bpyCH$_2$NEt$_2$)Re(CO)$_3$(Py)](OTf). A solution of AgOTf (263 mg, 1.02 mmol) in 5 mL of THF was added to a solution of (bpyMe)Re(CO)$_3$Cl (499 mg, 1.02 mmol) in 50 mL of CH$_2$Cl$_2$ to immediately give a cloudy yellow mixture. After stirring for 2 hours, the precipitate was removed by filtration and 100 mL of ethanol and 10.0 mL of pyridine were added to the yellow solution. This was heated at 50° C. for 17 hours without visual change. The solvent was removed under vacuum to give a bright yellow powder. Chromatography on silica with acetonitrile gave pure [(bpyMe)Re(CO)$_3$(py)](OTf) as a yellow powder (555 mg, 80%). $^1H$ NMR: δ 8.91 (d, 2H, J=5.7 Hz), 8.59 (s, 2H), 8.18 (d, 2H, J=5.2 Hz), 7.83 (t, 1H, 7.7 Hz), 7.54 (d, 2H, 5.5 Hz), 7.37 (t, 2H, 7.0 Hz), 2.62 (s, 6H). $^{13}C\{^1H\}$ NMR: δ 196.0, 191.5, 155.6, 154.9, 152.1, 151.8, 140.0, 129.7, 127.3, 126.7, 21.8. ESIMS: m/z 533.9 (M)$^+$. IR: $v_{CO}$=2034, 1932 cm$^{-1}$.

[(bpyN)Re(CO)$_3$(py)](OTf). The reaction of AgOTf(154 mg, 0.599 mmol) and (bpyN)Re(CO)$_3$Cl (363 mg, 0.596 mmol), followed by chromatography on silica with 1:2 toluene:acetonitrile gave pure [(bpyN)Re(CO)$_3$(Py)](OTf) as a yellow powder (260 mg, 54%). $^1H$ NMR: δ 8.96 (d, 1H, J=5.7 Hz), 8.90 (d, 1H, J=5.7 Hz), 8.61 (s, 1H), 8.52 (s, 1H), 8.18 (d, 2H, J=5.2 Hz), 7.84 (d, 1H, J=5.6 Hz), 7.81 (t, 1H, J=Hz), 7.54 (d, 1H, J=5.6 Hz), 7.36 (t, 2H, J=7.2 Hz), 7.32 (t, 2H, J=7.5 Hz), 7.24 (t, 1H, J=7.2 Hz), 3.85 (s, 2H), 3.66 (s, 2H), 2.65 (s, 3H), 2.31 (s, 3H). $^{13}C\{^1H\}$ NMR: δ 196.0, 195.9, 191.3, 156.7, 155.8, 155.5, 154.9, 152.4, 152.2, 151.8, 140.0, 138.5, 129.8, 129.2, 128.6, 128.3, 127.6, 127.3, 126.8, 125.4, 62.5, 59.9, 43.0, 21.9. ESIMS: m/z 652.9 (M)$^+$. IR: $v_{CO}$=2034, 1931 cm$^{-1}$.

[(bpyNB)Re(CO)$_3$(py)](OTf). The reaction of AgOTf (115 mg, 0.448 mmol) and (bpyNB)Re(CO)$_3$Cl (292 mg, 0.447 mmol), followed by chromatography on basic alumina with 9:1 acetonitrile:methanol gave pure [(bpyNB)Re(CO)$_3$(py)](OTf) as a yellow powder (182 mg, 45%). $^1H$ NMR: δ 8.94 (d, 1H, J=5.7 Hz), 8.90 (d, 1H, J=5.6 Hz), 8.36 (s, 1H), 8.24 (s, 1H), 8.18 (d, 2H, J=5.1 Hz), 7.79 (t, 1H, J=7.7 Hz), 7.65 (d, 1H, J=5.6 Hz), 7.62 (d, 1H, J=5.6 Hz), 7.53 (d, 1H, J=7.3 Hz), 7.35 (t, 2H, J=7.0 Hz), 7.14 (m, 2H), 7.06 (m, 1H), 3.86 (d, 2H, J=12.8 Hz), 3.73 (s, 4H), 3.63 (q, 2H, J=15.0 Hz), 2.64 (s, 3H), 2.38 (s, 3H), 0.98 (s, 6H). $^{13}C\{^1H\}$ NMR: δ 195.7, 195.6, 191.4, 155.9, 155.3, 155.2, 154.3, 152.4, 152.3, 151.8, 144.1, 139.9, 135.9, 133.9, 130.0, 129.4, 129.0, 128.7, 127.2, 126.8, 126.1, 125.4, 72.4, 62.4, 59.6, 44.5, 31.9, 21.9, 21.7. ESIMS: m/z 697.2 (unprotected M)$^+$. IR: $v_{CO}$=2034, 1931 cm$^{-1}$.

[(bpyMe)Ru(bpyF)$_2$]Cl$_2$. The compounds [(bpyMe)Ru(bpyF)$_2$]Cl$_2$, [(bpyN)Ru(bpyF)$_2$]Cl$_2$, and [(bpyNB)Ru(bpyF)$_2$]Cl$_2$ were all prepared in a manner similar to [(bpy)Ru(bpyF)$_2$]Cl$_2$(bpy=2,2'-bipyridine). A mixture of Ru(bpyF)$_2$Cl$_2$ (232 mg, 293 mmol) and bpyMe (112 mg, 608 mmol) in 50 mL of MeOH was heated at reflux for 16 hours to give a dark purple mixture. The solvent was removed under vacuum and the crude brown material purified by chromatography on basic alumina. Impurities eluted off first as blue and pink bands with acetonitrile. Elution of the final orange band with methanol gave pure [(bpyMe)Ru(bpyF)$_2$]Cl$_2$ (144 mg, 52%) as an orange powder upon solvent removal. $^1$H NMR (CD$_3$CN): δ 9.35 ('t', 4H, J=7.7 Hz), 8.60 (s, 2H), 8.47 (m, 4H), 7.98 (s, 2H), 7.88 (s, 2H), 7.52 (d, 2H, J=5.8 Hz), 7.29 (d, 2H, J=5.7), 2.54 (s, 6H). $^{13}$C{$^1$H} NMR (CD$_3$CN): δ 160.8, 160.5, 157.3, 152.8, 152.7, 150.6, 149.7, 136.9, 136.8, 130.8 (q, J=19.8 Hz), 130.5 (q, J=19.7 Hz), 129.5, 128.2, 127.9, 126.6, 124.2, 122.0, 21.3. ESIMS: m/z 435 [M]$^{2+}$, 870 [M]$^+$.

[(bpyN)Ru(bpyF)$_2$]Cl$_2$. The reaction of Ru(bpyF)$_2$Cl$_2$ (171 mg, 216 mmol) and bpyN (133 mg, 438 mmol) gave pure [(bpyN)Ru(bpyF)$_2$]Cl$_2$ (180 mg, 79%) as an orange powder upon solvent removal. $^1$H NMR (d$_6$-acetone): δ 10.18 (m, 4H), 9.30 (s, 1H), 9.25 (s, 1H), 8.62 (m, 4H), 8.48 (d, 2H, J=6.4 Hz), 8.29 (s, 1H), 8.20 (s, 1H), 8.07 (d, 2H, J=5.8 Hz), 8.00 (d, 2H, J=5.8 Hz), 7.67 (d, 2H, J=7.57 Hz), 7.48 (d, 2H, J=5.7 Hz), 7.35 (d, 2H, J=7.2 Hz), 7.28 (t, 2H, J=7.5 Hz), 7.22 (t, 1H, J=7.24 Hz), 3.84 (s, 2H), 3.59 (s, 2H), 2.61 (s, 3H), 2.56 (s, 3H). $^{13}$C{$^1$H} NMR (d$_6$-acetone): δ 161.5, 161.0, 160.9, 157.9, 157.5, 153.9, 153.4, 152.9, 152.4, 150.3, 149.4, 149.2, 139.8, 137.0, 136.8, 130.4 (q, J=19.1 Hz), 130.1 (q, J=19.3 Hz), 129.7, 129.4, 129.2, 128.5, 128.0, 127.1, 125.9, 124.2, 122.1, 62.5, 60.2, 42.4. ESIMS: 494.5 m/z [M]$^{2+}$.

[(bpyNB)Ru(bpyF)$_2$]Cl$_2$. The reaction of Ru(bpyF)$_2$Cl$_2$ (216 mg, 273 mmol) and bpyNB (226 mg, 544 mmol), followed by chromatography in basic alumina with 10% methanol/acetonitrile gave pure [(bpyNB)Ru(bpyF)$_2$]Cl$_2$ (283 mg, 89%) as an orange powder upon solvent removal. $^1$H NMR (d$_6$-acetone): δ 8.60 (d, 2H, J=4.9 Hz), 8.53 (d, 2H, J=5.0 Hz), 8.46 (s, 2H), 8.32 (s, 1H), 7.58 (d, 1H, J=6.9 Hz), 7.35 (m, 3H), 7.31–7.19 (m, 7H), 3.80 (s, 4H), 3.74 (s, 2H), 3.65 (s, 2H), 2.42 (s, 3H), 2.20 (s, 3H), 1.03 (s, 6H). $^{13}$C{$^1$H} NMR (d$_6$-acetone): δ 156.9 (q, J=26.3 Hz), 150.3, 150.2, 149.9, 149.8, 148.7, 144.3, 142.8, 137.0, 134.0, 131.5, 130.5, 129.9, 129.5, 129.3, 128.6, 127.9, 127.2, 125.6, 125.5, 125.0, 122.4, 122.2, 122.0, 119.9, 116.6, 72.7, 62.3, 60.6, 42.3, 32.5, 22.3, 21.2. ESIMS: m/z 1033.2 (unprotected M)$^+$, 516.6 (unprotected M)$^{2+}$.

Synthesis Discussion

Figure 17:
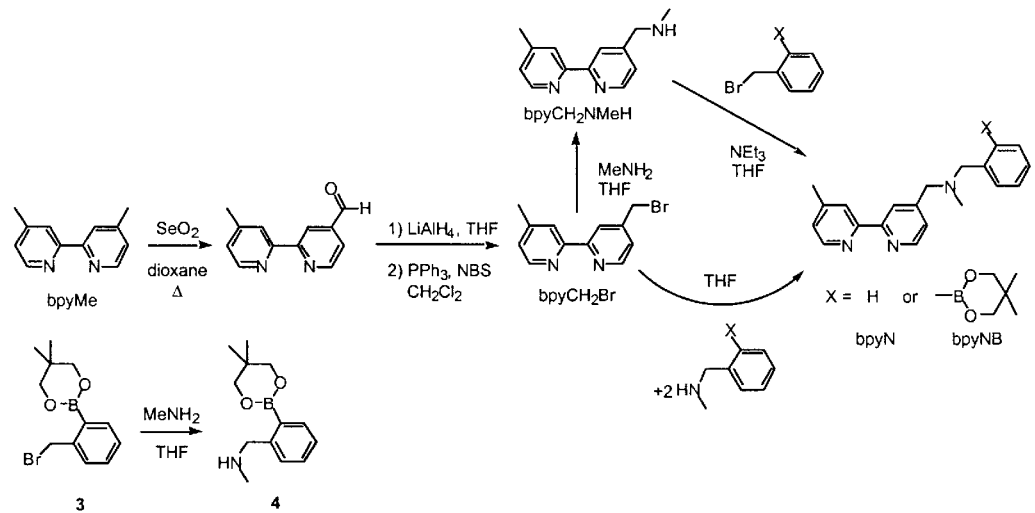
FIG. 17 shows a scheme for the synthesis of typical boronate and benzyl bipyridine ligands of the invention.
Figure 18:
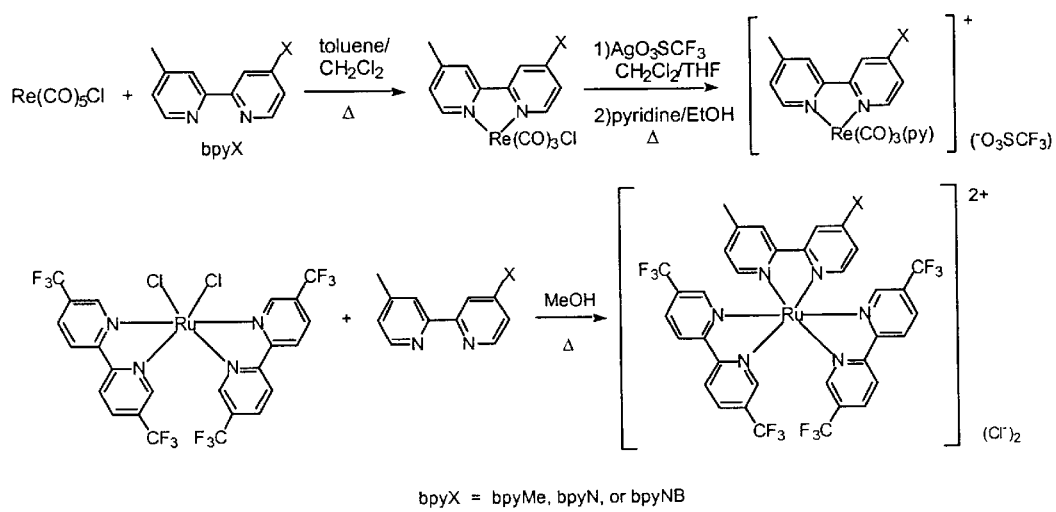
FIG. 18 shows a scheme for the preparation of typical transition metal complexes of the invention.

Bipyridine Ligand Synthesis. Typical compounds of the invention include the new boronate and benzyl bipyridine ligands which can be synthesized by the routes shown in FIG. 17. The common intermediate to both sets of transition metal complexes prepared in this work is the bipyridyl boronate ligand bpyNB. Previous work by Meyer (see e.g. Meyer, T. J. *Account Chem Res* 1989, 22, 163–170) and others has shown that compound bpyCH$_2$Br provides the simplest entry into a variety of functionalized bipyridine compounds. While the preparation of bpyCH$_2$Br can only be carried out in moderate yields, the final two alkylation steps generally occur in 70–80% yield, allowing multigram batches of bpyN or bpyNB to be conveniently prepared. The use of 3 was introduced by Shinkai as a useful reagent for appending the o-tolylboronic acid group to fluorophores such as ArCH$_2$NMeH (Ar=phenyl, naphthyl, anthryl). We have prepared the amino boronate reagent 4, which can also be used in the synthesis of bpyNB. In this case, either the linear or convergent route gives acceptable results, although in other systems we have found 3 or 4 to be more convenient depending on the transformation required. Rhenium Complex Synthesis. The rhenium complexes [(bpyX)Re(CO)$_3$Cl] and [(bpyX)Re(CO)$_3$(py)](OTf) (bpyX=bpyMe, bpyN, and bpyNB) were prepared as shown in FIG. 18 using the bipyridyl ligands bpyMe, bpyN, and bpyNB. These reactions are analogous to previous reports and can be carried out in high yield (see e.g. Li et al., *Chem Phys Lipids* 1999, 99, 1–9). The three ligand derivatives were prepared for both rhenium and ruthenium in order to aid in the interpretation of the fluorescence and electrochemical data discussed below. The $^1$H and $^{13}$C{$^1$H} NMR spectra and MS data clearly confirm the identity of the compounds. IR spectra of the three chloro complexes, [(bpyX)Re(CO)$_3$Cl] (bpyX= bpyMe, bpyN, and bpyNB), each exhibit carbonyl stretches at 2022, 1917, at 1895 cm$^{-1}$; CO resonances are observed at 2034 and 1931 cm$^{-1}$ for each of the pyridium complexes [(bpyX)Re(CO)$_3$(Py)](OTf). These data are in exact accord with the reported values for[(bpyCH$_2$NEt$_2$)Re(CO)$_3$Cl] (OTf) (2021, 1917, at 1895 cm$^{-1}$) and [(bpyCH$_2$NEt$_2$)Re(CO)$_3$(py)](OTf) (2034 and 1931 cm$^{-1}$). It is worth noting that the carbonyl stretching frequencies don't vary among the set of chloro compounds or among the set of pyridinium complexes. This suggests that the substituent changes on the periphery of the bipyridyl ligands do not substantially alter the electron density at the metal center (see electrochemistry below). Ruthenium Complex Synthesis. The syntheses of ruthenium bipyridine derivatives [(bpyX)Ru(bpyF)$_2$]Cl$_2$ (bpyX=bpyMe, bpyN, and bpyNB) were carried out following the reactions shown in FIG. 18. This procedure is analogous to that of Furue et al, which involves the direct combination of RuCl$_2$(bpyF)$_2$ with excess bipyridine ligand in refluxing methanol. The NMR and mass spectra clearly indicate the synthesis of the desired products. Attempts to carry out the reaction by the more common procedure of chloride abstraction with silver triflate followed by addition of the bipyridine derivative failed to yield the desired products (Gould et al., *Inorg Chem* 1991, 30, 2942–2949). This is presumably due to unwanted side reactions involving fluoride abstraction by Ag$^+$ from the trifluoromethylated bipyridyl ligands of RuCl$_2$(bpyF)$_2$.

Electrochemistry. The search for new fluorescent glucose transducers based on PET requires, among other things, an understanding of the electrochemistry of any potential donor-acceptor pair. The free energy of PET ($\Delta G_{e1}$) can be calculated using the Rehm-Weller equation shown in eq 1, where E$^0$(D$^+$/D) is the oxidation potential of the $$\Delta G_{e1}(\text{kcal mol}^{-1}) = 23.06[E^0(D^+/D) - E^0(A/A^-)] - w_p - w_r - \Delta G_{00} \quad (1)$$

donor, E$^0$(A/A$^-$) is the reduction potential of the acceptor, and $\Delta G_{00}$ is the free energy corresponding to the equilibrium energy E$_{00}$. The quantities w$_p$ and w$_r$ are Coulombic terms for the products and reactants, and are found to be small in polar solvents. In our case, w$_r$=0 since the reactants are neutral. To simplify predictions, we assume w$_p$ to be zero and estimate E$_{00}$ as the energy corresponding to [$\lambda_{max}$(ex)+ $\lambda_{max}$(em)]/2 for each fluorophore. While more accurate E$_{00}$ values can be found in the literature for anthracene, [Ru(bipy)$_3$]$^{2+}$, and a number of other compounds, we find this crude method of calculation useful for estimating equilibrium energies for new compounds that have not been previously reported.

Thus, in our present systems, the measurement of the first reduction potential for the transition metal complexes [(bpyNB)Re(CO)$_3$(Py)](OTf) (−1.25 V vs. Ag/AgCl) and [(bpyNB)Ru(bpyF)$_2$]Cl$_2$ (−0.85 V vs. Ag/AgCl) and the first oxidation potential of the N-methyl amine functional group (1.26 V vs. Ag/AgCl) metal complexes gives estimated $\Delta G_{e1}$ values of −5.0 kcal mol$^{-1}$ and −3.8 kcal mol$^{-1}$, respectively. In considering these values, it is worth comparing them to $\Delta G_{e1}$ for 1 as shown in FIG. 15. For 1, the first oxidation potential and reduction potential are 1.10 V and −2.11 V vs, Ag/AgCl, respectively. With excitation and emission maxima at 369 nm and 420 nm for 1, the calculated $\Delta G_{e1}$ is 1.5 kcal mol$^{-1}$. The fact that this value is greater than zero would suggest that PET is not be favorable, which is seemingly in conflict with the experimental observation that it does occur. Therefore, we stress that our estimates of $\Delta G_{e1}$ shouldn't be considered as accurate in an absolute sense, but taken as a measure of the relative driving force for PET. Thus, we suggest that PET in compounds [(bpyNB)Re(CO)$_3$(Py)](OTf) and [(bpyNB)Ru(bpyF)$_2$]Cl$_2$ is approximately 5–6 kcal mol$^{-1}$ more favorable than for 1. It is useful to note that these predictions could be made prior to compound synthesis using literature electrochemical and fluorescence data for the parent compounds [(bpy)Ru(bpyF)$_2$]Cl$_2$ and [Re(bpy)(CO)$_2$(Py)](OTf). This is why a derivative of the more unusual bis(trifluoromethyl)bipyridine complex [(bpy)Ru(bipy$^F$)$_2$]Cl$_2$ was prepared, rather than the more common parent complex [Ru(bpy)$_3$]Cl$_2$ (−0.77 V vs. SCE and −1.31 V vs. SCE, respectively). These reduction potentials would yield expected $\Delta G_{e1}$ values of −3.8 kcal mol$^{-1}$ and 12.5 kcal mol$^{-1}$, respectively.

Fluorescence Spectroscopy, pH Switching.

The most direct test of the validity of these calculations is to examine the response of these compounds to pH changes. At high pH, the pendant amine group is expected to quench fluorescence; by protonation of the amine at low pH, quenching should not occur, giving maximum fluorescence. This has been the basis for a number of previous molecular transducers for pH detection, including bipyridine complexes of ruthenium and rhenium. In our case, the modulation of amine quenching by an attached glucose-boronate complex is more complex and more difficult to predict than modulation of this effect by a proton or alkali metal. Understanding the nature of the boron-nitrogen interaction is crucial in the development of a better glucose transducer by this approach.

Initial tests of fluorescence switching due to pH changes were examined to determine the optimal response for these systems. The emission and excitation spectra for [(bpyX)Re(CO)$_3$(Py)](OTf) and [(bpyX)Ru(bpyF)$_2$]Cl$_2$ (bpyX= bpyMe, bpyN, bpyNB) in aqueous solution showed little variation in the respective series (for [(bpyX)Re(CO)$_3$(Py)](OTf) $\lambda_{ex}/\lambda_{em}$=361 nm/552 nm, for [(bpyX)Ru(bpyF)$_2$]Cl$_2$) $\lambda_{ex}/\lambda_{em}$=450 nm/635 nm). As expected for compounds without a pendant amine functionality, the relative fluorescence of [(bpyMe)Re(CO)$_3$(py)](OTf) and [(bpyMe)Ru(bpyF)$_2$]Cl$_2$ remained constant over the pH range of 2 to 11. Compounds [(bpyN)Re(CO)$_3$(Py)](OTf) and [(bpyN)Ru(bpyF)$_2$]Cl$_2$ were then examined under these conditions and relative fluorescence intensities of 10.3:8.5:1 and 2.15:1.1:1 were measured. Thus a drop from pH 7 to pH 2 gave a signal increase of 21% and 95% for the rhenium and ruthenium complexes. These numbers are indicators of the maximum signal expected from glucose switching in the corresponding boronate complexes [(bpyNB)Re(CO)$_3$(py)](OTf) and [(bpyNB)Ru(bpyF)$_2$]Cl$_2$. The level of fluorescence at pH 7 corresponds to the signal expected in the absence of glucose (physiological pH 7.4); the level of fluorescence at pH 2 corresponds to the signal expected at high glucose concentration. On the other hand, when the pH is changed from 11 to 2, a much greater change in fluorescence is observed (930% for rhenium and 115% for ruthenium). While the eventual use of a molecular transducer for glucose will dictate operation at physiological pH, these data places limits on the greatest fractional increase in signal that could be expected from PET sensors based on these fluorophores. Shinkai has suggested that by the appropriate choice of boronate and structural motif, the pK$_a$ of the amine could be altered to take advantage of the full light output possible from a given fluorophore. Furthermore, the greater fractional switching observed for complex [(bpyNB)Re(CO)$_3$(py)](OTf) vs. [(bpyNB)Ru(bpyF)$_2$]Cl$_2$ is consistent with our expectations based on the Rehm-Weller equation discussed above.

One way of examining the effect of amine pK$_a$ is through the comparison of [(bpyNB)Re(CO)$_3$(py)](OTf) with the known compound (bpyCH$_2$NEt$_2$)Re(CO)$_3$(Py)](OTf). The bpyCH$_2$NEt$_2$ derivative exhibits a 61% increase in fluorescence upon changing pH from 11 to 2 (the signal is essentially the same at pH 2 and 7). This is significantly less than that measured for [(bpyN)Re(CO)$_3$(py)](OTf) (930% increase). Considering that the two compounds have nearly the same oxidation potentials (1.35 V and 1.34 V vs. Ag/AgCl) and exactly the same reduction potentials of −1.20 V vs. Ag/AgCl, this difference in behavior does not appear to be electronic in origin, but rather due to steric differences between the two amino groups.

Glucose Testing.

Figure 19:
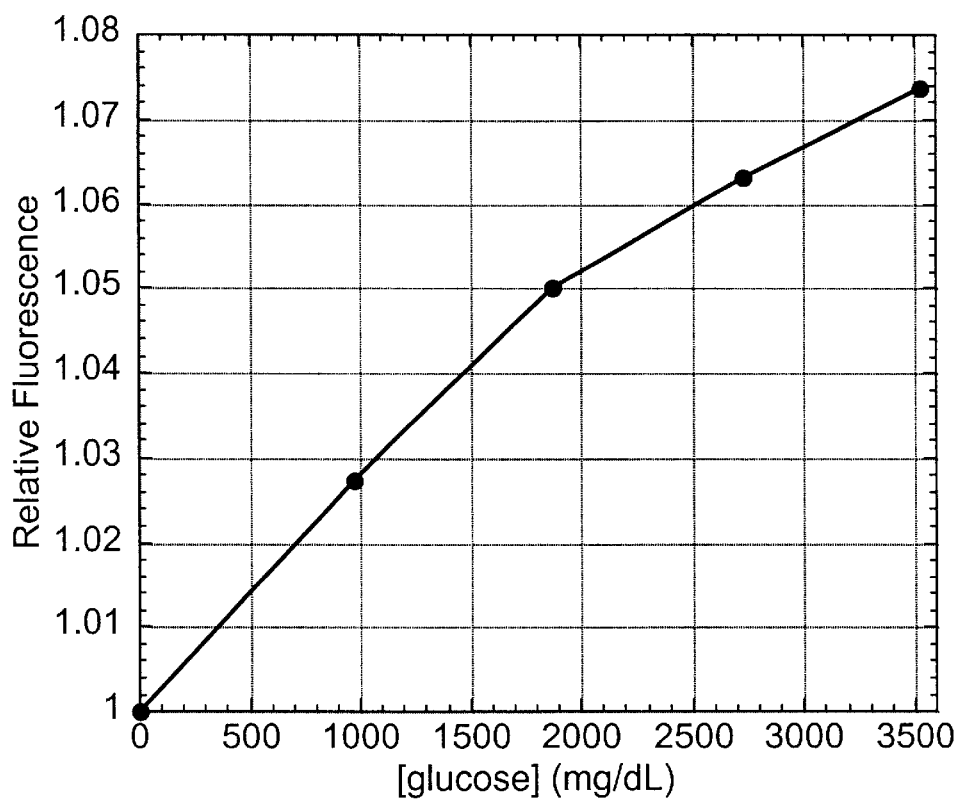
FIG. 19 shows the relative fluorescence intensity of 10.0 $\mu$M [(bpyNB)Ru(bpyF)$_2$]Cl$_2$ in 50:50 MeOH:PBS vs. [glucose] with $\lambda_{ex}/\lambda_{em}$=450 nm/635 nm.

The first important control tests were to confirm that compounds [(bpyX)Re(CO)$_3$(py)](OTf) and [(bpyX)Ru(bpyF)$_2$]Cl$_2$ (bpyX=bpyMe and bpyN) did not respond to increases in glucose from 0 up to about 3600 mg/dL. (The region of greatest physiological interest is approximately 25–350 mg/dL.) In addition to these control compounds, the rhenium boronate complex [(bpyNB)Re(CO)$_3$(py)](OTf) showed no fluorescence response to glucose levels, while the ruthenium boronate complex [(bpyNB)Ru(bpyF)$_2$]Cl$_2$ did. A plot of relative fluorescence vs. glucose concentration is shown in FIG. 19. While we do observe the desired signal increase with increasing glucose concentration, the response is quite moderate (7% increase from 0 to 3000 mg/dL of glucose). This level of response is substantially less than the nearly 200% relative fluorescence increase observed by Shinkai for 1 over the same concentration range, however nearly identical to that seen in Akkaya's squaraine system (8% increase) (Kukrer, B.; Akkaya, E. U. *Tetrahedron Lett* 1999, 40, 9125–9128) and similar to magnitude to Czarnik's anthracene boronates (8% decrease) (see e.g. Yoon, J.; Czarnik, A. W. *J Amer Chem Soc* 1992, 114, 5874–5875). This loss in fractional switching is partially compensated by the increased transmission of visible light through the skin at longer wavelength in [(bpyNB)Ru(bpyF)$_2$]Cl$_2$ and in Akkaya's compound (Kukrer, B.; Akkaya, E. U. *Tetrahedron Lett* 1999, 40, 9125–9128), as well as their increased water solubility. Clearly, better systems must be found for the transduction of glucose at longer wavelengths. For our purposes, it was worthwhile to demonstrate that we could design a new small molecule transducer for glucose by a rational approach based on initial studies of electrochemistry and fluorescence properties, thus saving on the time spent trying to synthesize new saccharide transducers. Using the disclosure provided herein, the results obtained from this work can be applied to the development of improved sensors for glucose.

Summarized Synthesis of Ru(N-Methyl Benzyl Boronate)

1. Ligand Synthesis (a) 4-carbaldehyde-4'-methyl-2,2'-bipyridine: 4,4'-dimethylbipyridine was refluxed overnight with one equivalent of SeO$_2$ in 1,4-dioxane. The solution was filtered while still hot, and cooled to room temperature for an hour. The cream-colored precipitate was removed by filtration and the solvent pumped dry. The crude solid was extracted with ethyl acetate, washed with sodium carbonate solution, and then extracted with sodium bisulfite. The pH of this solution was adjusted to 9 with sodium carbonate, and the solution extracted with dichloromethane. The combined organic extracts were dried with magnesium sulfate and the solution pumped dry to a pure white powder. Yields 30%. $^1$H NMR spectra are consistent with structure.

(b) 4-hydroxymethyl-4'-methyl-2,2'-bipyridine: A slurry of lithium aluminum hydride in THF was added dropwise in slight excess to a solution of 4-carbaldehyde-4'-methyl-2,2'-bipyridine in THF at −40° C. Stirring was continued for about an hour, until the temperature rose to about −20° C. The solution was then cooled again to about −40° C. and quenched with 10% aqueous THF. The reaction was warmed to room temperature, filtered, and pumped dry to a yellow powder. Yields 75%. $^1$H NMR spectra are consistent with structure.

(c) 4-bromomethyl-4'-methyl-2,2'-bipyridine: To a solution of crude 4-hydroxymethyl-4'-methyl-2,2'-bipyridine in methylene chloride at 0° C. were added a slight excess of both $PPh_3$ and N-bromosuccinimide to immediately give a brown-orange solution. The mixture was stirred for 1 h, warmed to room temperature, and concentrated to a thick brown oil. Chromatography on silica with 1:1 hexanes-:diethyl ether as eluent gave the product as a white powder. Yields 50%. $^1$H NMR spectra are consistent with structure.

(d) 4-methylaminomethyl-4'-methyl-2,2'-bipyridine: Methylamine was bubbled slowly through a solution of 4-bromomethyl-4'-methyl-2,2'-bipyridine in THF for 10 min at 0° C. to give a white precipitate and a colorless solution. After bubbling, the solution was stirred for another hour at room temperature. The reaction was pumped dry to a pale off-white wax. The wax was extracted with diethyl ether and pumped dry to a pale yellow oil. Yields 80%. $^1$H NMR spectra are consistent with structure.

(e) Neopentylglycol protected o-bromomethylphenylboronic acid. Prepared by a method described in the literature: Hawkins, et al., J. Am. Chem. Soc. 82:3863 (1960) and James, et al., J. Am. Chem. Soc. 117:8982 (1995).

(f) 4-[N-o-methylphenylboronic neopentylglycol ester] methylaminomethyl-4'-methyl-2,2'-bipyridine: A solution of 4-methylaminomethyl-4'-methyl-2,2'-bipyridine in acetonitrile was added dropwise over 10 min to an equimolar solution of neopentylglycol protected o-bromomethylphenylboronic acid and triethylamine in acetonitrile to give a pale yellow solution that was stirred for 1 h at room temperature. The solution was pumped dry to an off-white waxy solid. A colorless solution was extracted from a cream-colored powder with diethyl ether, and pumped dry to a cream-colored waxy solid. Yields 75%. $^1$H NMR spectrum is consistent with structure. 2. Ruthenium Complex Synthesis (a) 5,5'-bistrifluoromethyl-2,2'-bipyridine ($bipy^F$) was synthesized for the preparation of ruthenium complexes using a literature procedure. The substituted bipyridine ligands are used to shift metal complex redox potential so that PET becomes viable.

(b) The parent compound, Ru(5,5'-bistrifluoromethyl-2,2'-bipyridine)$_2$Cl$_2$, was made by refluxing RuCl$_3$ with 5,5'-bistrifluoromethyl-2,2'-bipyridine in DMF. This was used to prepare the bis($bipy^F$) ruthenium complexes.

(c) (4-[N-o-methylphenylboronic neopentylglycol ester] methylaminomethyl-4'-methyl-2,2'-bipyridine)Ru(5,5'-bistrifluoromethyl-2,2'-bipyridine)$_2$Cl$_2$: A mixture of Ru(5,5'-bistrifluoromethyl-2,2'-bipyridine)$_2$Cl$_2$ and 4-[N-o-methylphenylboronic neopentylglycol ester] methylaminomethyl-4'-methyl-2,2'-bipyridine (1:2 molar ratio) in methanol were refluxed for 2 days to give a dark orange-brown solution. This was pumped dry to a dark brown solid. Chromatography was carried out by gradient elution using acetonitrile:methanol. The blue and pink-purple bands were discarded and the third orange band collected. It was pumped dry to a dark orange-brown powder. Yield 90%. Identity of products verified by $^1$H and $^{13}$C NMR spectra and GC-MS.

Example 2

Conjugated Organic Heterocyclic Ring System Fluorophores

Figure 10:
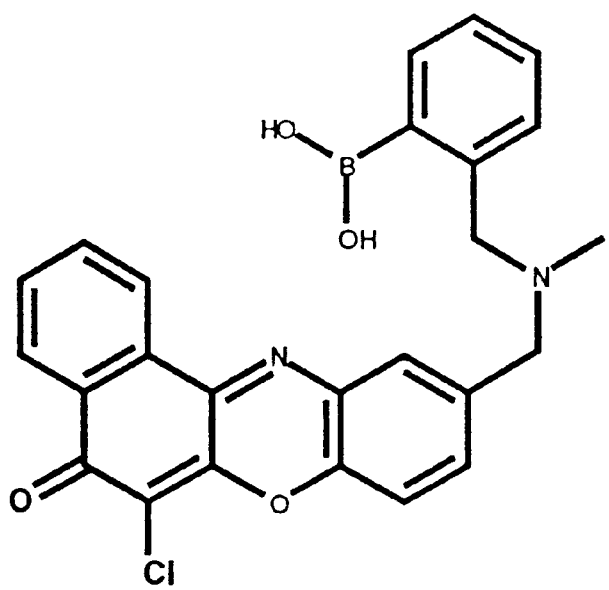
FIG. 10 shows chloro-oxazine-5-one boronate.
Figure 11:
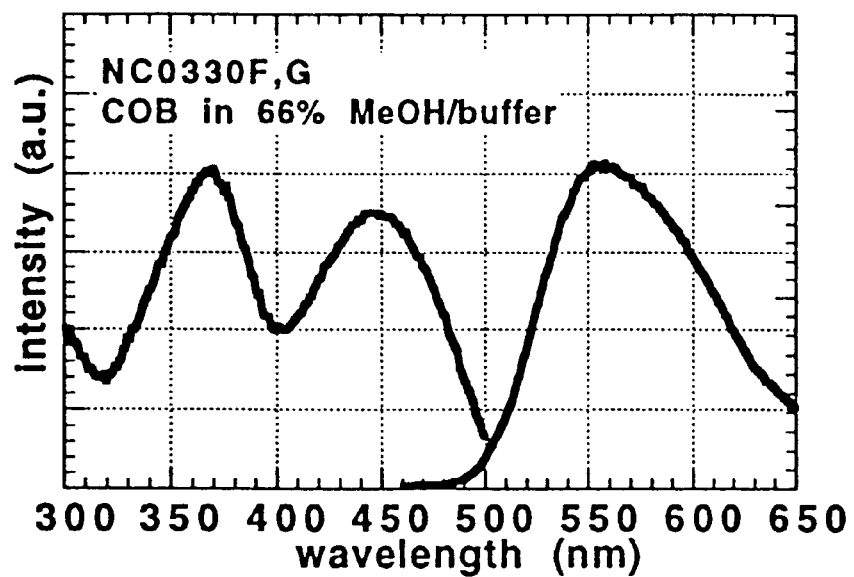
FIG. 11 shows the excitation and emission spectra obtained for a sample of chloro-oxazine-5-one boronate in methanol/buffer.

To investigate the conjugated organic heterocyclic ring system compounds as fluorophores, an oxazine-one system was studied. An oxazine-one is described as a neutral (uncharged) precursor to a charged oxazine dye. The final compound (fluorophore+switch+recognition site) named chloro-oxazine-one boronate (COB) is shown in FIG. 10. The relevant values for the COB system for the Rehm-Weller equation are: $\Delta G_{PET}$=−12.1 kcal/mole, $E^0(Z^{ox})$=0.88V, $E^0(F^{red})$=−1.10V, and $\Delta E_{00}$=57.8 kcal/mole. The compound's response to glucose in several solvent systems was characterized. A stock solution of the compound was prepared by dissolving 5.7 mg in 5 mL of methanol. Samples were prepared by adding 30 μL of this stock solution to 3 mL of solvent. Three solvent mixtures were used: (1) pure methanol (MeOH), (2) 66% MeOH by volume in pH 7.4 buffer, and (3) 25% MeOH by volume in pH 7.4 buffer. FIG. 11 shows the excitation and emission spectra obtained for a sample of the oxazine-one compound in 66% MeOH/buffer. Based on these spectra, excitation and emission wavelengths of 450 nm and 560 nm respectively were chosen for subsequent steady-state fluorescence tests; however, emission wavelengths in excess of 600 nm would also be satisfactory for monitoring the fluorescence intensity. The 450 nm excitation band is well-matched to commercially available ultrabright LED emitters.

Figure 12:
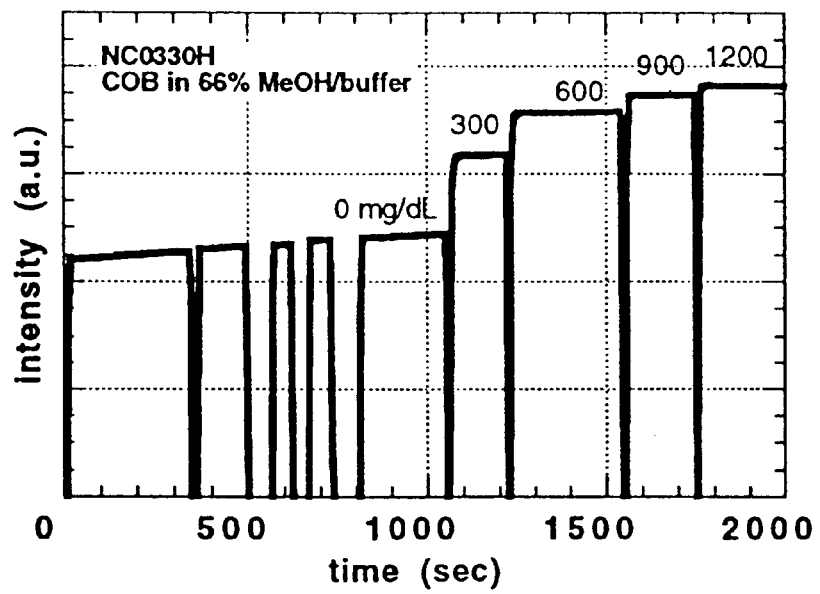
FIG. 12 shows results of adding glucose to chloro-oxazine-5-one boronate.

Glucose sensitivity testing was performed on the oxazine-one compound. Samples were prepared as described above and titrated with 30 μL aliquots of concentrated glucose solution (300 mg/mL). Each aliquot raised the glucose concentration of the sample by about 300 mg/dL. FIG. 12 shows the results of an experiment performed with a 66% MeOH/buffer solvent. Following an initial period in which the baseline fluorescence level was determined, four 30 μL aliquots of glucose were introduced into the sample resulting in a final glucose concentration of approximately 1200 mg/dL. In this solvent system, glucose transduction yields a 45% increase in the fluorescence intensity as the glucose concentration is increased from zero to 600 mg/dL. This is a switching fraction similar to that exhibited by anthracene boronate, but now the transduction has been achieved well within the green (for the emission), where a several-fold improvement in the optical transport efficiency of human skin is realizable.

Figure 13:
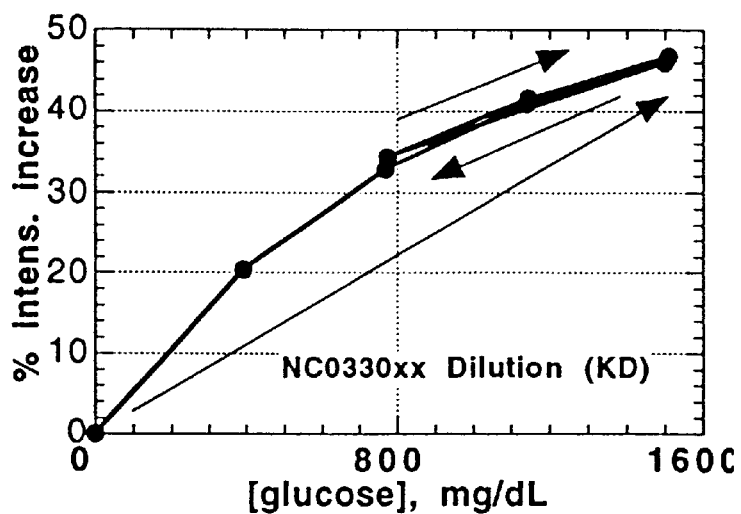
FIG. 13 shows the results of a glucose reversibility experiment.

The reversibility of the glucose transduction was experimentally investigated. Samples, 1.5 mL in volume, were prepared as described above in 3.5 mL cuvettes (including stir bar volume). Concentrated glucose is added in increments to bring the glucose concentration to about 1500 mg/dL. The glucose concentration is then halved by adding 1.5 mL of solvent. The glucose concentration is then increased in increments as before. FIG. 13 shows the results of one glucose-cycle experiment. Over the range tested, there is full reversibility of the glucose response. These results show that it is not necessary to synthesize an oxazine; its oxazine-one precursor can be used.

A. Synthesis of A Benzophenoxazinone Boronate

Figure 20:
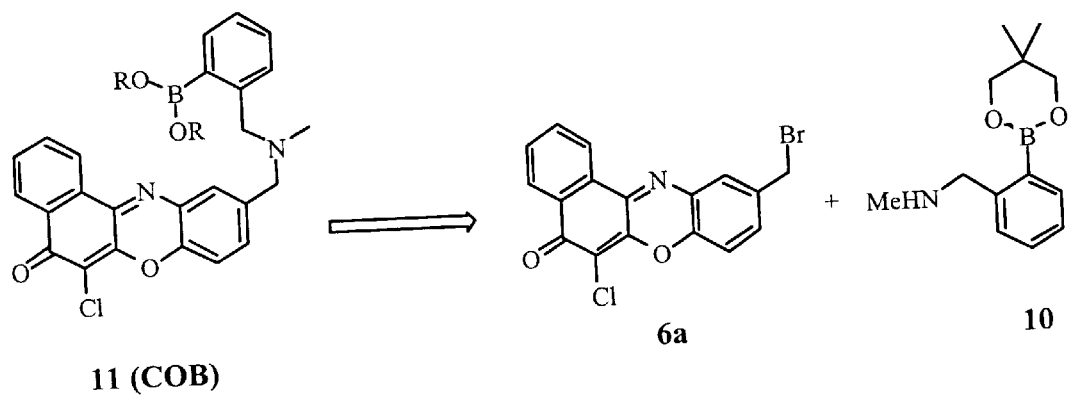
FIG. 20 shows a scheme pertaining to the synthesis of COB (Chloro-Oxazine Boronate) and is shown below as benzophenoxazinone 11. COB was constructed by coupling benzophenoxazinone 6a with phenyl boronate 10 via a methylene amine linkage.

As an illustrative molecular assembly of a typical compound for use in glucose recognition, the synthesis of 6-chloro-5H-benzo[a]phenoxazin-5-one boronate 11 (as shown in FIG. 20) is shown below. As discussed in detail above, this strategy involves the synergistic integration of three main components: a fluorophore, a selective glucose binding unit, and a transducer. The benzo[a]phenoxazin-5-one ring system was incorporated as the fluorophore because it possess many desirable characteristics including high quantum yields, excitation maxima accessible to simple light sources, chemical and photochemical stability. For the glucose binding unit, an aromatic boronic acid group was employed since it has been shown that they have selective recognition for saccharides. These two main components are attached via a methylene amine tether. In this case, the amine serves not only as a linker but is an integral part of the glucose sensing design. The target sensor molecule, 6-chloro-5H-benzo[a]phenoxazin-5-one boronate 11, is based on fluorescent signaling via photoinduced electron transfer. The PET process in this unique system is modulated by interaction of boronic acid and amine.

Synthesis

The target molecule for glucose recognition is abbreviated as COB (Chloro-Oxazine Boronate) and is shown below as benzophenoxazinone 11. COB was constructed by coupling benzophenoxazinone 6a with phenyl boronate 10 via a methylene amine linkage (as shown in FIG. 20).

Figure 21:
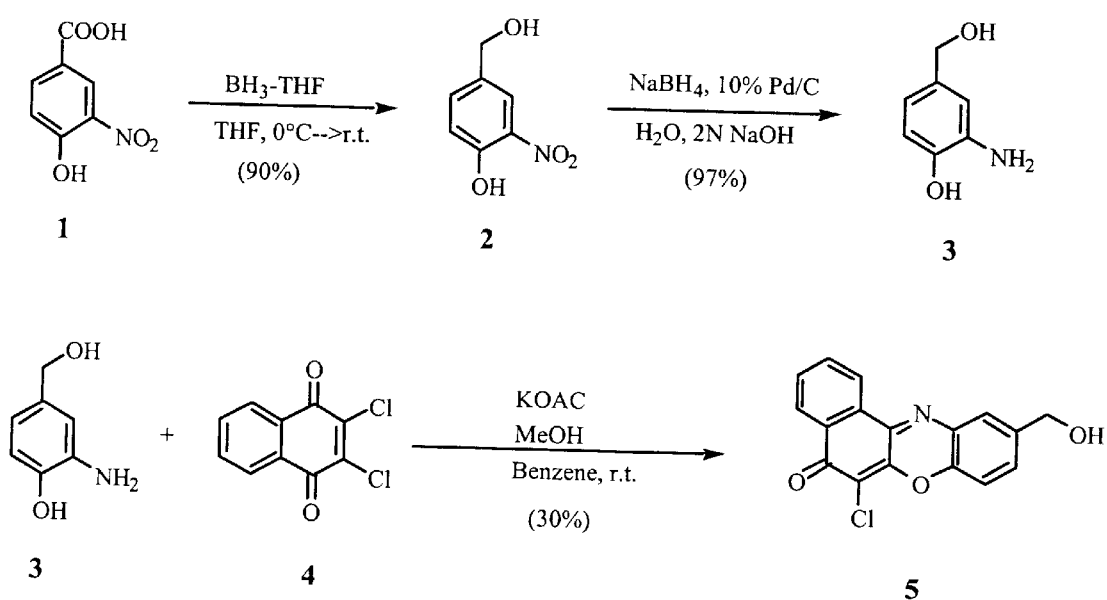
FIG. 21 shows a scheme pertaining to the synthesis of COB (Chloro-Oxazine Boronate) and is shown below as benzophenoxazinone 11. Benzophenoxazinone 6a was synthesized by condensation of 3-amino-4-hydroxybenzyl alcohol 3 with 2,3-dichloro-1,4-napthoquinone 4.

Benzophenoxazinone 6a was synthesized by condensation of 3-amino-4-hydroxybenzyl alcohol 3 with 2,3-dichloro-1,4-napthoquinone 4 (FIG. 21). The preparation of amino alcohol 3 required successive reductions from commercially available 4-hydroxy-3-nitrobenzoic acid 1. Reduction of benzoic acid 1 with borane-THF complex in tetrahydrofuran gave 4-hydroxy-3-nitrobenzyl alcohol 2 in 90% yield. Subsequent reduction of nitro-alcohol 2 with sodium borohydride and 10% Pd/C catalyst in water provided 3-amino-4-hydroxybenzyl alcohol 3 in 97% yield. The reductions were followed by ring forming condensation of 3-amino-4-hydroxybenzyl alcohol 3 with 2,3-dichloro-1,4-naphthoquinone 4. The reaction was performed in a methanol/benzene solvent mixture using potassium acetate at room temperature. The condensation required dropwise addition of a suspension of amino alcohol 3 and potassium acetate in methanol to a slurry of quinone 4 in benzene resulting in 6-chloro-10-(hydroxymethyl)-5H-benzo[a]phenoxazin-5-one 5 in 30% yield. Initially, the condensation was investigated using methanol and potassium hydroxide. These conditions produced a complex mixture of products, some of which may have resulted from reaction of potassium hydroxide with napthoquinone 4.

Figure 22:
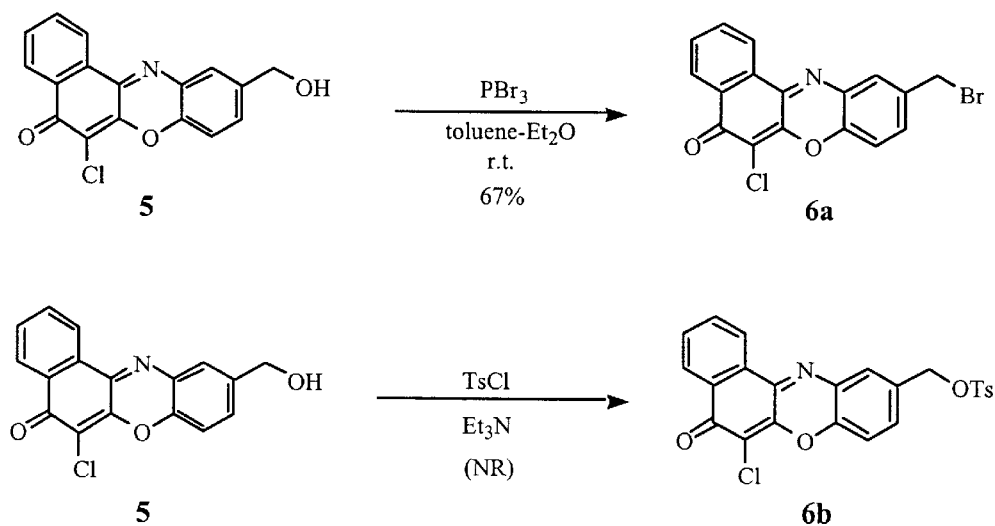
FIG. 22 shows a scheme pertaining to the synthesis of COB (Chloro-Oxazine Boronate). After ring condensation, benzophenoxazinone 5 was then converted to the benzophenoxazinone bromide 6 using phosphorous tribromide in an ether/toluene solvent mixture at room temperature.

After ring condensation, benzophenoxazinone 5 was then converted to the benzophenoxazinone bromide 6 using phosphorous tribromide in an ether/toluene solvent mixture at room temperature (FIG. 22). These conditions provided 6-chloro-10-(bromomethyl)-5H-benzo[a]phenoxazin-5-one 6a in 67% yield. Alternatively, tosylate formation from benzophenoxazinone 5 using triethylamine and tosyl chloride did not produce the desired tosylate 6b.

Figure 23:
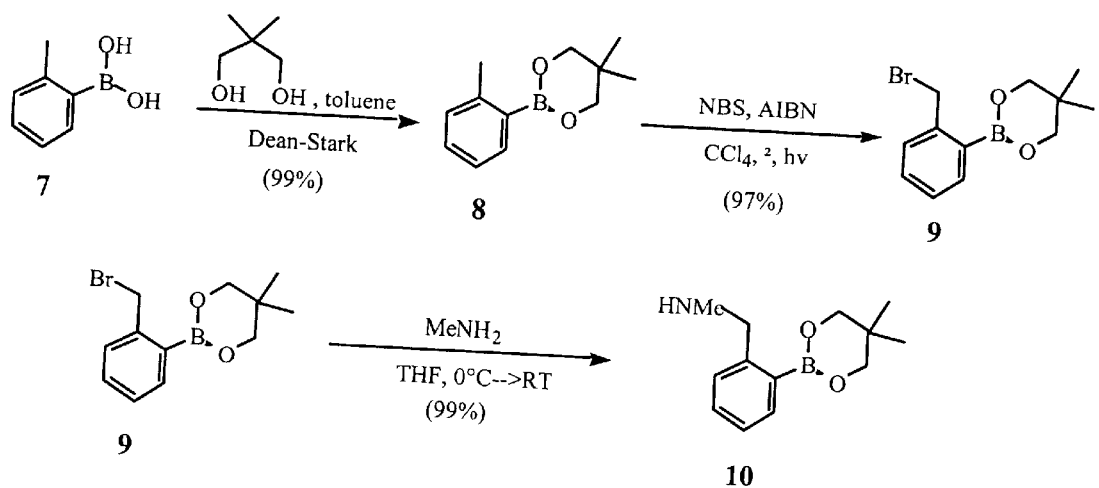
FIG. 23 shows a scheme pertaining to the synthesis of COB (Chloro-Oxazine Boronate). An amino boronate derivative 10 was synthesized by bubbling methylamine through a etheral solution of phenyl boronate 9. Methylaminophenyl boronate 10 was isolated cleanly in 99% yield.

Nevertheless, benzophenoxazinone bromide 6a had been prepared and now required attachment with the glucose binding boronate unit. The preparation of the benzophenoxazinone coupling partner, aminophenyl boronate 10, required protection of o-tolylboronic acid 7 with neopentyl glycol to give the corresponding o-tolylboronic ester 8 in 99% yield. Boronic ester 8 was functionalized by free radical bromination using N-bromosuccinimide in carbon tetrachloride and AIBN as the initiator. The reaction conditions required heating, as well as, irradiation with a light source to give bromomethylphenyl boronate 9 in 97% yield. Subsequently, amino boronate derivative 10 was synthesized by bubbling methylamine through a etheral solution of phenyl boronate 9. Methylaminophenyl boronate 10 was isolated cleanly in 99% yield (FIG. 23).

Figure 24:
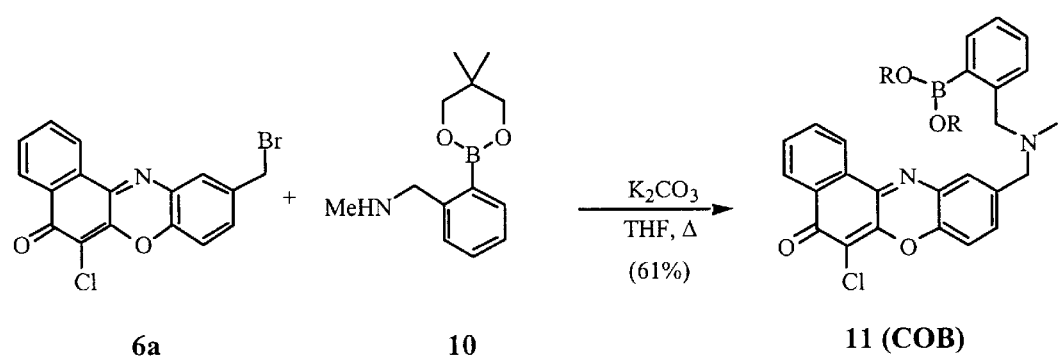
FIG. 24 shows a scheme pertaining to the synthesis of COB (Chloro-Oxazine Boronate). For completion of the COB synthesis, coupling of the aminophenyl boronate 10 and benzophenoxazine 6a was preformed in refluxing tetrahydrofuran using potassium carbonate for four days. The target benzophenoxazine 11 was purified by chromatography and isolated as solid in 61% yield.

For completion of the COB synthesis, coupling of the aminophenyl boronate 10 and benzophenoxazine 6a was preformed in refluxing tetrahydrofuran using potassium carbonate for four days (FIG. 24). The target benzophenoxazine 11 was purified by chromatography and isolated as solid in 61% yield.

Fluorescence Measurements/Glucose Transduction

COB's response was evaluated in several solvent systems. For our studies, a stock solution of the COB was prepared by dissolving 5.7 mg in 5 ml of methanol. Samples were prepared by adding 30 $\mu$L of this stock solution to 3 mL of solvent. Three solvent mixtures were used: (1) pure MeOH, (2) 66% MeOH by volume in pH 7.4 buffer, and (3) 25% MeOH by volume in pH 7.4 buffer. FIG. 11 shows the excitation and emission spectra obtained for a sample of the COB compound in 66% MeOH/buffer.

Based on these spectra, excitation and emission wavelengths of 450 nm and 560 nm, respectively, were chosen for subsequent steady-state fluorescence tests. However, it should be mentioned that emission wavelengths in excess of 600 nm would also be satisfactory for monitoring the fluorescence intensity and that the 450 nm excitation band is quite well matched to currently available ultra-bright LED emitters. Samples, prepared as above, were titrated with 30 $\mu$L aliquots of concentrated glucose solution (300 mg/mL). Roughly speaking, each aliquot raised the glucose concentration of the sample by about 300 mg/dL. FIG. 12 shows the results of the experiment performed with a 66% MeOH/buffer solvent. Following an initial period in which the baseline fluorescence level was determined, four 30 $\mu$L aliquots of glucose were introduced into the sample resulting in a final glucose concentration of approximately 1200 mg/dL. In this solvent system, glucose transduction yielded a 45% increase in the fluorescence intensity as the glucose concentration is increased from zero to 600 mg/dL. These results showed that we have successfully designed a glucose recognition system based on fluorescent signaling.

As shown above, the design of a typical sort of glucose recognition compounds disclosed herein was completed by the synthesis of 6-chloro-5H-benzo[a]phenoxazin-5-one boronate 11. This system incorporates unique features that enable its' application as a successful glucose sensor. The premise for our sensor is based on fluorescent signaling induction via photoinduced electron transfer, which is modulated by interaction of boronic acid and amine. Initially studies revealed that varying glucose concentrations had a significant effect on fluorescence intensities. These results provide evidence that there is great promise in using the COB system as a fluorescent glucose sensor. Also, using the teachings disclosed herein, modifications of COB can be investigated in order to optimize signal transduction.

Example 3

Naphthalimide Fluorophores

This presentation provides results on the development of such a system based on the illustrative naphthalimide boronate compounds shown and described in FIGS. 25–29. These compounds offer the benefits of having high quantum yields, longer wavelength operation, and relatively high water solubility compared to previously reported transducers. We have synthesized compounds with attachment groups for incorporation into a polymer, and will discuss the electrochemistry of these systems as in pertains to predicting improved sensor molecules.

Synthesis.

Figure 25:
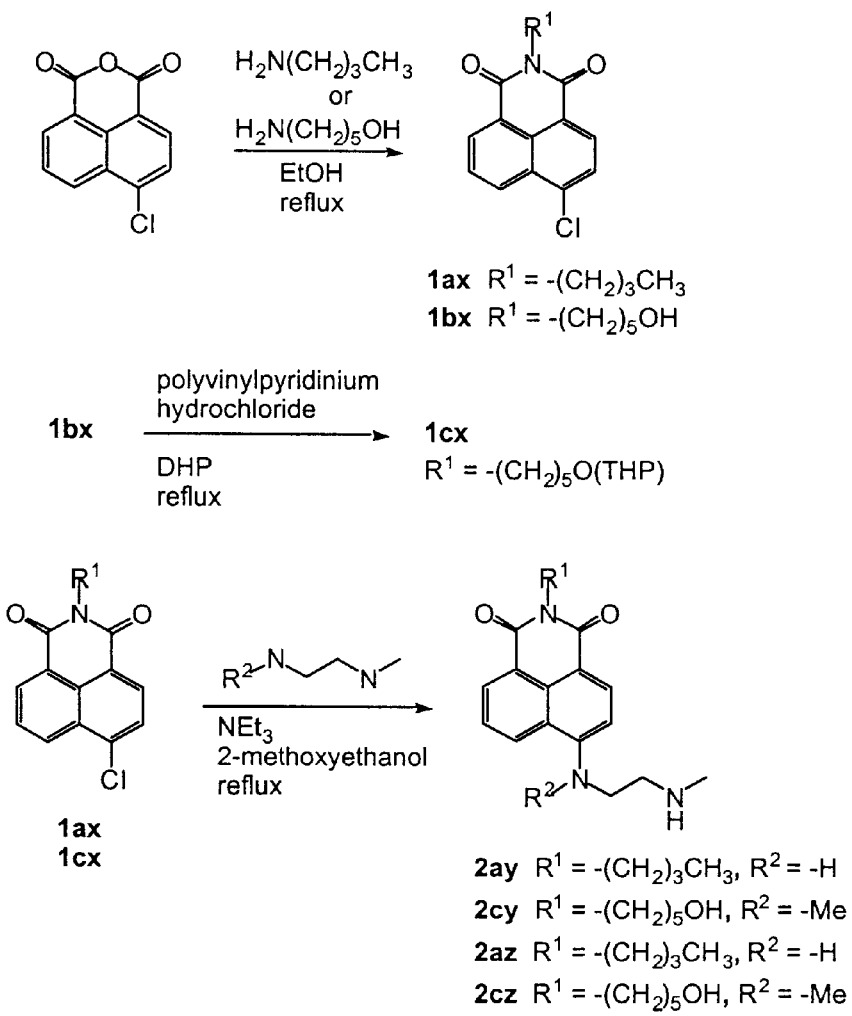
FIG. 25 shows a scheme pertaining to the synthesis of the napthalamide boronate transducer derivatives taught in Example 3.
Figure 26:
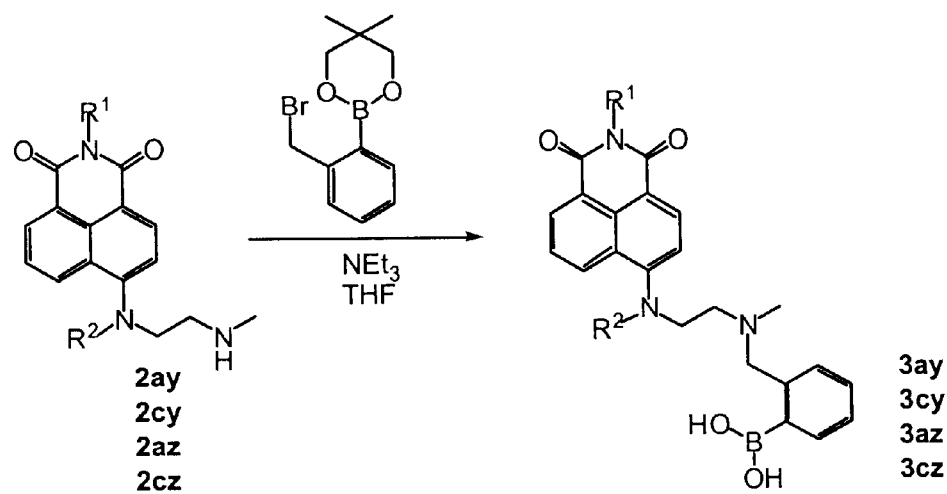
FIG. 26 shows a scheme pertaining to the synthesis of the napthalamide boronate transducer derivatives as taught in Example 3.
Figure 26:
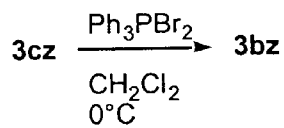

The naphthalimide derivatives studied in this project were prepared by the routes shown in FIGS. 25 and 26. These procedures are analogous to those previously reported for naphthalimide dye molecules, with some distinctions (see e.g. Alexiou et al., *J. Chem. Soc., Perkin Trans.* 1990, 837; de Silva et al., *Angew. Chem. Int. Ed. Engl.* 1995, 34, 1728; Kavarnos, G. J. *Fundamentals of Photoinduced Electron Transfer*; VCH: New York, 1993; pp 37–40. and Daffy et al. *Chem. Eur. J.* 1998, 4, 1810). The naphthalimide framework has been shown to exhibit a wide range of spectral properties, depending on the alkyl groups appended to the imide nitrogen and the 4-position. Most work to date has used an n-butyl group off the imide nitrogen (e.g. 1ax)., generally giving rise to high quantum yields than shorter or unsaturated side chains. In order to covalently link these molecules to polymer matrices, we have also prepared derivatives based on a 5-pentanol linker starting with the preparation of 1bx. To enable further functionalization of these dye molecules, it was necessary to protect the pendant alcohol as the tetrahydropyranyl (THP) ether.

Substitution of the 4-chloro group by either N-methylethylene diamine or N,N'-dimethylethylene diamine gave the desired compounds 2ay, 2cy, 2az, and 2cz in good yields. The reaction involving the unsymmetric N-methylethylene diamine gave exclusively substitution at the primary amine end of the ethylenediamine species. It has been shown that the quantum yields for dyes based on secondary naphthylamines are substantially higher that those observed for tertiary amines; however, it was believed that further functionalization might be simplied on the tertiary compounds. Thus, both sets of compounds were prepared for examination by fluorescence spectroscopy.

Work by de Silva has shown the utility of similar compounds as fluorescent transducers for pH. Based on our previous work, and that of Shinkai (see e.g. James et al., *J. Am. Chem. Soc.* 1995, 117, 8982), we have appended a benzyl boronate group from the terminal amine group to give compounds 3ay, 3cy, 3az, and 3cz in good yields. The spectroscopy of these compounds is discussed below. In order to enable the attachment of this system to polymers, deprotection of the pendant THP ether gave the free alcohol, which is suitable for conversion to a number of other functional groups. Preparation of the amine derivative is in progress.

Fluorescence Measurements and Analysis

Fluorescence Spectra and Relative Quantum Yields.

Figure 27:
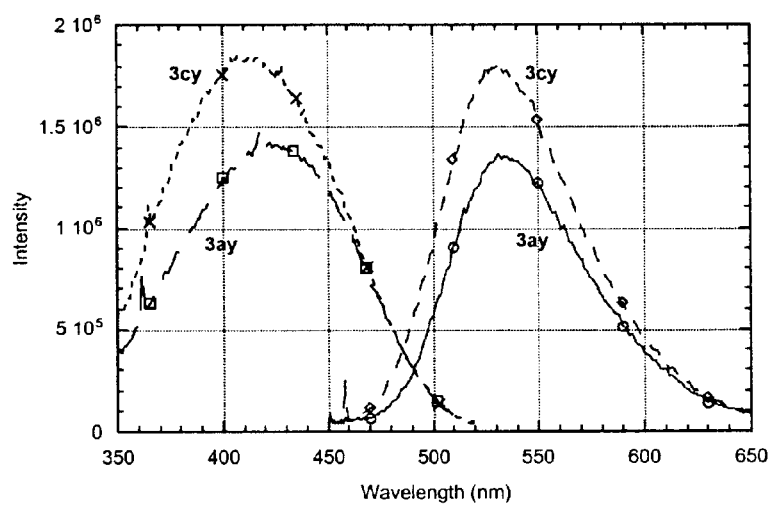
FIG. 27 shows sample excitation and emission spectra of typical napthalamide boronate transducer derivatives as taught in Example 3 (3ay and 3cy).
Figure 28:
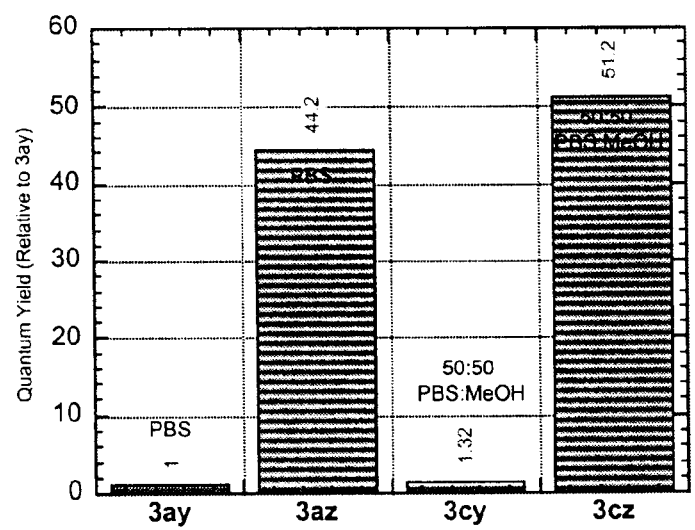
FIG. 28 shows relative quantum yields of typical napthalamide boronate transducer derivatives as taught in Example 3.

Sample excitation and emission spectra are shown in FIG. 27 for 3ay and 3cy, along with fluorescence maxima in Table 1. Literature references indicate a higher quantum yield for secondary-amine naphthalimide derivatives than for tertiary amines in otherwise similar compounds. The pragmatic value of this gain was examined, weighing synthetic difficulty against measurable relative quantum yields. The results are shown in FIG. 28 and Table 1 below.

TABLE 1

Spectroscopic parameters for 3 in PBS buffer (pH 7.4).

| | Excitation $\lambda_{max}$ | Emission $\lambda_{max}$ | Relative Quantum Yield | Fluorescence Intensity Increase with added glucose (0 to 600 mg dL$^{-1}$) | (Quantum Yield) * (Fluorescence Increase) |
|---|---|---|---|---|---|
| 3ay | 420 nm | 535 nm | 1 | 16% | 16% |
| 3cy | 415 nm | 525 nm | 1.32 | 13% | 17% |
| 3az | 435 nm | 535 nm | 44.2 | 9% | 398% |
| 3cz | 435 nm | 525 nm | 51.2 | 10% | 512% |

The two compounds with secondary amino groups have quantum yields of 40–50 times that of the tertiary compounds, making them clearly superior choices for sensing purposes. Removal of the THP protecting group from compound 3cz shows no significant change in quantum yield or wavelength maximum.

In addition to quantum yield changes, there are small but significant shifts in the fluorescence wavelengths for these compounds. The compounds with secondary amines have somewhat longer excitation wavelengths (435 nm) than the corresponding tertiary compounds (415 nm and 420 nm). In addition, the compounds functionalized with THP ethers have emission spectra shifted 10 nm towards the red of the butyl imide derivatives (535 nm vs. 525 nm).

Glucose Testing.

Figure 29:
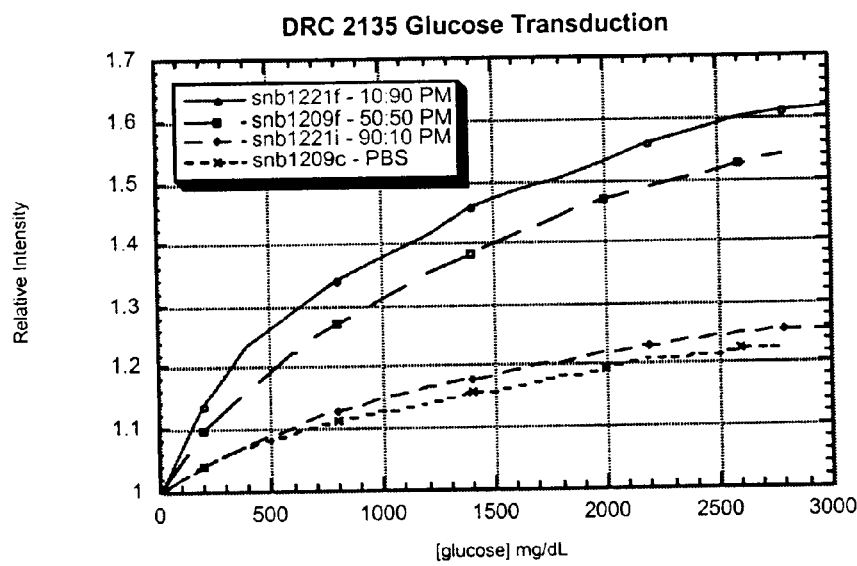
FIG. 29 shows the fluorescence spectra (relative fluorescence vs. [glucose]) of typical napthalamide boronate transducer derivatives taught in Example 3, specifically 3ay in a range of solvent mixtures (10:90, 50:50, 90:10 and 100:0 PBS:MeOH).

The fluorescence spectra of compounds 3 have been obtained as a function of increasing glucose concentration. This data is shown in FIG. 29 for compound 3ay and fractional fluorescence intensity increases for compounds 3 are listed in Table 1. These values range from 9% to 16% over the four compounds, with the two lower values coming from the two compounds having secondary amino groups. These low values of fractional switching are more than balanced out by the high quantum yields for compounds 3az and 3cz. As a measure of the total signal increase for each system, the product of quantum yield and fractional fluorescence increase are given in Table 1, showing that 3cz is the most promising sensor candidate of the group, as expected.

The fluorescence response of these compounds shows a strong dependence on solvent composition in methanol/PBS mixtures, with greater methanol concentration corresponding to increased fluorescent emission. This trend is similar to that observed in other systems in our laboratories and is shown in FIG. 29 for the compound 3ay.

Electrochemistry.

Reduction and oxidation potentials were measured for compounds 3ay, 3cy, 3az, and 3cz using cyclic voltammetry (Table 2). By using the Rehm-Weller equation (eq 1), $$\Delta G_{e1} = 23.06[E^0(D^-/D) - E^0(A/A^-)] - \Delta G_{00} \quad (1)$$

it is possible to estimate the free energy of photoinduced electron transfer (PET) in these systems (see e.g. Kavarnos, G. J. *Fundamentals of Photoinduced Electron Transfer*; VCH: New York, 1993; pp 37–40). $E^0(D^+/D)$ and $E^0(A/A^-)$ correspond to the reduction potential and oxidation potential of the electron donor (i.e. amine) and electron acceptor (i.e. fluorophore), respectively. The quantity $\Delta G_{00}$ is the equilibrium energy, which we estimate as the energy corresponding to the equilibrium wavelength $\lambda_{00}$. As an estimate of $\lambda_{00}$, we use the average of the excitation and emission maxima for each fluorophore. Smaller solvent-dependent work terms for the Coulombic interaction between the reactants and products are left out for simplicity. Since the mechanism of fluorescence switching in these systems depends on PET, this gives us a rough estimate of which fluorophores should give the best response to glucose.

TABLE 2

Electrochemical data and estimates of free energy for PET.

| Compound | Amine Oxidation Potential E° (D$^+$/D) (V) | Fluorophore Reduction Potential E° (A/A$^-$) (V) | $\lambda_{00}$ (nm) | $\Delta G_{PET}$ (kcal mol$^{-1}$) |
|---|---|---|---|---|
| 3ay | 0.91 | −1.48 | 478 | −4.8 |
| 3cy | 0.93 | −1.47 | 470 | −5.5 |
| 3az | 1.05 | −1.48 | 485 | −0.62 |
| 3cz | 1.00 | −1.53 | 480 | −1.2 |

Although these calculations are quite simple, the more positive $\Delta G_{pet}$ values found for 3az and 3cz, with secondary amino groups, correspond to the compounds with a lower fractional increase in fluorescence. The most striking differences in Table 2 are in the amine oxidation potentials, which are significantly higher for the secondary amines vs. the tertiary amines. As explained above, this weaker fractional response is offset by the far greater signal output (quantum yield) for compounds 3az and 3cz. Equally important is that we can use this sort of simple calculation to improve upon and search for new molecular transducers for glucose.

Synythesis

Summarized Syntheses. As the syntheses are described as a series of analogous compounds with general procedures are given below. Cyclic voltammetry was conducted using a glassy carbon working electrode, platinum counter electrode, and Ag/AgCl reference electrode and carried out in a 0.1 M solution of NBu$_4$ClO$_4$ in acetonitrile. Samples for fluorescence were prepared as 1.00 mM stock solutions in MeOH. A 30.0 μL aliquot of solution was then added to 3.000 mL of the appropriate solvent mixture (a combination of methanol and phosphate buffered saline—PBS). Relative quantum yields were determined by the relative output of equimolar solutions of two compounds using 3ay as a reference. Glucose additions were performed by the addition of a concentrated solution of glucose in PBS to a stirred solution of the fluorescent molecule in methanol/PBS.

1ax, 1bx. A equimolar mixture of 4-chloro-1,8-naphthalic anhydride and either n-butylamine or 5-aminopentanol in ethanol was heated at reflux for 20 hours. The dark brown solution was filtered and cooled to −10° C. A pure, tan powder was collected by filtration (90% yield). The identities of the pure products were confirmed by $^1$H and $^{13}$C{$^1$H} NMR spectroscopy, as well as ESI/MS (electrospray ionization mass spectrometry).

1cx. A mixture of 1bx and catalytic (10 mol %) poly(4-vinylpyridinium hydrochloride) was heated at reflux in neat 3,4-dihydro-2H-pyran for over 16 hours. The reaction was cooled and the polymer removed by filtration. Removal of solvent under vacuum gave the product as an orange colored oil, which was purified by chromatography on silica gel with chloroform as eluent. The product was collected as a pure orange oil in quantitative yield. The identity of the pure product was confirmed by $^1$H and $^{13}$C{$^1$H} NMR spectroscopy, as well as ESI/MS.

2ay, 2cy, 2az, 2cz. Excess N,N'-dimethylethylenediamine or N'-methylethylenediamine were added to a solution of either 1ax or 1cx, followed by the addition of one equivalent of triethylamine. This solution was heated at reflux for 4 hours in 2-methoxyethanol to give a dark brown-orange solution. The reaction was cooled, water added, and the product extracted with dichloromethane. Drying with magnesium sulfate, followed by solvent removal, gave the crude product as an orange oil. Purification of 2az was achieved by recrystallization from hot methanol; the other compounds were purified by chromatography on silica with a methanol/chloroform gradient. The products were obtained as yellow powders or orange oils in 60–70% yield. The identities of the pure products were confirmed by $^1$H and $^{13}$C {H} NMR spectroscopy, as well as ESI/MS.

2ay, 2cy, 2az, 2cz. Excess N,N'-dimethylethylenediamine or N'-methylethylenediamine were added to a solution of either 1ax or 1cx, followed by the addition of one equivalent of triethylamine. This solution was heated at reflux for 4 hours in 2-methoxyethanol to give a dark brown-orange solution. The reaction was cooled, water added, and the product extracted with dichloromethane. Drying with magnesium sulfate, followed by solvent removal, gave the crude product as an orange oil. Purification of 2az was achieved by recrystallization from hot methanol; the other compounds were purified by chromatography on silica with a methanol/chloroform gradient. The products were obtained as yellow powders or orange oils in 60–70% yield. The identities of the pure products were confirmed by $^1$H and $^{13}$C{(H} NMR spectroscopy, as well as ESI/MS.

3ay, 3cy, 3az, 3cz. One equivalent of 2,2-dimethylpropane-1,3-diyl[o-(bromomethyl)phenyl] boronate in THF was added dropwise to an equimolar solution of 2ay, 2cy, 2az, or 2cz and triethylamine in THF. After stirring 2 hours, the solvent was removed and the crude oil purified by chromatography on silica with a methanol/ammonium hydroxide gradient. The products were collected in 60–80% yield as yellow powders. The identities of the pure products were confirmed by $^1$H and $^{13}$C{$^1$H} NMR spectroscopy, as well as ESI/MS.

Detailed Synthesis

General. All reactions were performed under an atmosphere of N$_2$, followed by work-up in air. Protected boronate esters were stored under vacuum to prevent slow hydrolysis from atmospheric moisture. Unless stated otherwise, all chemicals were purchased from commercial suppliers. Anhydrous solvents from Aldrich were used for all reactions. Starting compounds known in the art such as N-n-butyl-4-chloronaphthalene-1,8-dicarboximide(1ax), 2,2-dimethylpropane-1,3-diyl[o-(bromomethyl) phenyl] boronate, were prepared by literature methods (see e.g. Daffy et al. Chem-Eur J 1998, 4, 1810–1815; de Silva et al., Chem Rev 1997, 97, 1515–1566). Samples for FT IR spectroscopy were prepared as solutions in CHCl$_3$, and only the C=O stretches are reported here. All mass spectra were obtained using electrospray ionization (ESI/MS) with an ionization potential of 50V and a solvent system consisting of 1% acetic acid in 50/50 methanol/water. Cyclic voltammetry was conducted using a glassy carbon working electrode, platinum counter electrode, and Ag/AgCl reference electrode and carried out in a 0.1 M solution of NBu$_4$ClO$_4$ in acetonitrile. Samples for fluorescence measurements were prepared as 1.00 mM stock solutions in MeOH. A 30.0 μL aliquot of solution was then added to 3.000 mL of the appropriate solvent mixture (a combination of methanol and phosphate buffered saline—PBS) giving a final concentration of 10.0 μM for each complex. Changes in pH were carried out by the addition of small volumes of concentrated hydrochloric acid, acetic acid, or sodium hydroxide. Glucose additions were performed by the addition of a concentrated solution of glucose in PBS to a stirred solution of fluorophore in a cuvette. Relative quantum yield measurements were carried out by measuring the relative intensities of equimolar solutions (10.0 μM) of two fluorophores. Compound 3ay was used as the reference.

N-n-Butyl4-chloronaphthalene-1,8-dicarboximide (1ax): This compound has been reported previously. This preparation is similar to previously reports (see e.g. Daffy et al. *Chem-Eur J* 1998, 4, 1810–1815; de Silva et al., *Chem Rev* 1997, 97, 1515–1566). A portion of n-butylamine (5.00 mL, 50.6 mmol) was added to a suspension of 4-chloronaphthalene-1,8-dicarboximide (11.7 g, 50.5 mmol) in 160 mL of toluene. This mixture was brought to reflux for 17 hours to give a dark black-brown solution. Crystallization from hexanes/toluene at −10° C. gave 1ax as a pure brownish-yellow powder (11.1 g, 76%). $^1$H NMR: δ=8.65 (d, 1H, J=7.4 Hz), 8.58 (d, 1H, J=8.6 Hz), 8.49 (d, 1H, J=7.9 Hz), 7.85 (t, 1H, J=7.9 Hz), 7.81 (d, 1H, J=7.9 Hz), 4.18 (t, 2H, J=7.6 Hz), 1.72 (m, 2H), 1.45 (m, 2H), 0.98 (t, 2H, J=7.4 Hz). $^{13}$C{$^1$H} NMR: δ=163.8, 163.5, 139.0, 132.0, 131.2, 130.6, 129.3, 129.1, 127.9, 127.5, 123.2, 121.7, 40.5, 30.3, 20.5, 14.0. ESI/MS m/z.

N-(5'-Hydroxypentyl)-4-chloronaphthalene-1,8-dicarboximide (1bx): The procedure was analogous to 1ax. The reaction of 5-aminopentanol (5.15 g, 49.9 mmol) with 4-chloronaphthalene-1,8-dicarboximide (11.6 g, 49.9 mmol) in refluxing ethanol, followed by recrystallization from refluxing THF gave 1bx as a brownish-yellow powder (7.67 g, 48%). $^1$H NMR: δ 8.66 (d, 1H, J=7.6 Hz), 8.59 (d, 1H, J=8.3 Hz), 8.49 (d, 1H, J=8.0 Hz), 7.85 (t, 1H, J=7.9 Hz), 7.82 (d, 1H, J=8.0 Hz), 4.19 (t, 2H, J=7.5 Hz), 3.68 (t, 2H, J=6.4 Hz), 1.78 (m, 2H), 1.67 (m, 2H), 1.60 (br s, 1H), 1.51 (m, 2H). $^{13}$C{$^1$H} NMR: δ 164.0, 163.7, 139.3, 132.2, 131.4, 130.9, 129.5, 129.3, 128.1, 127.6, 123.3, 121.8, 63.0, 40.6, 32.6, 28.0, 23.5. ESI/MS m/z 318 (M+H)$^+$.

N-(5'-Hydroxypentyl)-4-bromonaphthalene-1,8-dicarboximide (1bx'): The procedure was analogous to 1ax. The reaction of 5-aminopentanol (3.90 g, 37.8 mmol) with 4-bromonaphthalene-1,8-dicarboximide (10.4 g, 37.6 mmol) in refluxing ethanol, followed by filtration and cooling to −10° C. gave 1bx' as a pale yellow powder (12.5 g, 92%). $^1$H NMR: δ 8.65 (d, 1H, J=7.7 Hz), 8.56 (d, 1H, J=8.0 Hz), 8.41 (d, 1H, J=8.0 Hz), 8.04 (d, 1H, J=7.8 Hz), 7.85 (t, 1H, J=7.9 Hz), 4.19 (t, 2H, J=7.5 Hz), 3.67 (t, 2H, 6.4 Hz), 1.78 (m, 2H), 1.66 (m, 2H), 1.56 (br s, 2H), 1.51 (m, 2H). $^{13}$C{$^1$H} NMR: δ=163.82, 163.79, 133.4, 132.2, 131.4, 131.3, 130.8, 130.4, 129.1, 128.3, 123.2, 122.3, 62.9, 40.6, 32.5, 28.0, 23.4. ESI/MS m/z xxx (M+).

N-(5'-Tetrahydropyranoxypentyl)-4-chloronaphthalene-1,8-dicarboximide (1cx): The was analogous to literature procedures. A mixture of 1bx (297 mg, 0.935 mmol), poly(4-vinylpyridinium hydrochloride) (20 mg, 0.13 mmol), and 10 mL of 3,4-dihydro-2H-pyran (DHP) was heated at reflux for 21 hours to give an orange solution. The solvent was removed under vacuum, giving an orange oil. Purification was carried out by chromatography on silica gel using chloroform as the eluent. Removal of solvent gave 1cx as a pure yellow oil (322 mg, 86%). $^1$H NMR: δ 8.60 (d, 1H, J=7.2 Hz), 8.52 (d, 1H, J=8.7 Hz), 8.43 (d, 1H, J=7.8 Hz), 7.80 (t, 1H, J=7.9 Hz), 7.76 (d, 1H, J=8.0 Hz), 4.56 (t, 1H, J=3.60 Hz), 4.15 (t,2H, J=7.6 Hz), 3.83 (m, 1H), 3.72 (m, 1H), 3.48 (m, 1H), 3.40 (m, 1H), 1.75 (m, 2H), 1.67 (m, 2H), 1.50 (m, 8H). $^{13}$C{$^1$H} NMR: δ=163.8, 163.5, 139.0, 132.1, 131.2, 130.6, 129.3, 129.1, 127.9, 127.5, 123.2, 121.7, 98.9, 67.4, 62.4, 40.6, 30.9, 29.6, 28.1, 25.7, 24.0, 19.8. ESI/MS m/z mess (M+).

N-(5'-Tetrahydropyranoxypentyl)-4-bromonaphthalene-1,8-dicarboximide (1cx'): The was analogous to literature procedures. A mixture of 1bx' (4.681 g, 12.9 mmol), poly(4-vinylpyridinium hydrochloride) (202 mg, 1.31 meq), and 30 mL of 3,4-dihydro-2H-pyran (DHP) was heated at reflux for 23 hours to give an orange solution. The solvent was removed under vacuum, giving an orange oil. Purification was carried out by chromatography on silica gel using chloroform as the eluent. Removal of solvent gave 1cx' as a beige waxy solid (5.231 g, 91%). $^1$H NMR: δ 8.62 (d, 1H, J=6.8 Hz), 8.52 (d, 1H, J=8.9 Hz), 8.37 (d, 1H, J=7.8 Hz), 8.01 (d, 1H, J=7.8 Hz), 7.82 (t, 1H, J=7.9 Hz), 4.57 (t, 1H, J=3.6 Hz), 4.16 (t, 2H, J=7.6 Hz), 3.84 (m, 1H), 3.74 (m, 1H), 3.49 (m, 1H), 3.40 (m, 1H), 1.77 (m, 4H), 1.67 (m, 2H), 1.51 (m, 6H). $^{13}$C{$^1$H} NMR: δ 163.71, 163.68, 133.3, 13.2.1, 131.3, 131.2, 130.7, 130.3, 129.1, 128.2, 123.3, 122.4, 98.9, 67.5, 62.4, 40.7, 30.9, 29.6, 28.1, 25.7, 24.0, 19.8. ESI/MS m/z mess (M+).

N-n-Butyl-4-(N'-methylaminoethylene-N"-methylamino)naphthalene-1,8-dicarboximide (2ay): A portion of N,N'-dimethyl-1,2-diaminoethane (2.00 mL, 18.8 mmol) was added to a suspension of 1ax (1.02 g, 3.55 mmol) in 20 mL of 2-methoxyethanol, followed by triethylamine (0.495 mL, 3.55 mmol) to immediately give a dark brown mixture. This mixture was brought to reflux for 4 hours to give a dark brown solution. After cooling to ambient temperature, 20 mL of water was added, the solution extracted with 3×30 mL dichloromethane, the organic layer dried with MgSO$_4$, and solvent removed under vacuum. The crude material was purified by chromatography on basic alumina with an acetonitrile/methanol gradient. The solvent was removed to give 2ay as a pure yellow powder (0.846 g, 70%). $^1$H NMR (CDCl$_3$): δ=8.58 ('t', 2H), 8.50 (d, 1H), 7.69 ('t', 1H), 7.24 (d, 1H), 4.18 (t, 2H), 3.46 (t, 2H), 3.06 (s, 3H), 2.94 (t, 2H), 2.47 (s, 3H), 1.71 (m, 2H), 1.46 (m +br, 4H), 0.98 (t, 3H). $^{13}$C{$^1$H} NMR: δ=164.6, 164.1, 156.6, 132.4, 131.1, 130.9, 130.2, 126.3, 125.5, 123.3, 116.1, 115.2, 56.4, 49.3, 42.1, 40.2, 36.7, 30.4, 20.5, 14.0. ESI/MS m/z 340 (M+H)$^+$.

N-n-Butyl-4-(N'-methylaminoethylamino)naphthalene-1,8-dicarboximide (2az): This was prepared analogously to 2ay. The reaction of 1ax (1.67 g, 5.82 mmol), N-methyl-1,2-diaminoethane (2.56 mL, 29.1 mmol), and triethylamine (0.811 mL, 5.82 mmol) in 2-methoxyethanol, followed by crystallization from hot methanol, yielded 2az as a pure yellow powder (1.44 g, 76%). $^1$H NMR (CDCl$_3$): δ=8.49 d, 1H, J=7.6 Hz), 8.37 (d, 1H, J=8.4 Hz), 8.09 (d, 1H, J=8.4 Hz), 7.53 (t, 1H, J=7.8 Hz), 6.60 (d, 1H, J=8.4 Hz), 6.25 (br, 1H), 4.14 (t, 2H, J=7.6 Hz), 3.39 (dd, 2H, J=4.9, 11.1 Hz), 3.03 (t, 2H, J=5.7 Hz), 2.50 (s, 3H), 1.70 (m, 2H), 1.43 (m, 2H), 0.96 (t, 3H, J=7.3 Hz). $^{13}$C{$^1$H} NMR: δ=164.8, 164.3, 149.8, 134.5, 131.1, 129.9, 126.4, 124.7, 123.1, 120.5, 110.3, 104.4, 49.7, 42.1, 40.1, 36.1, 30.5, 20.6, 14.0. ESI/MS m/z 326 (M+H)$^+$, 651 (2M+H)$^+$.

N-(5'-Tetrahydropyranoxypentyl)-4-(N'-methylaminoethylene-N"-methylamino)naphthalene-1,8-dicarboximide (2cy): This was prepared analogously to 2ay. The reaction of 1cx (0.271 g, 0.674 mmol), N,N'-dimethyl-1,2-diaminoethane (0.359 mL, 3.37 mmol), and triethylamine (94.0 μL, 0.674 mmol) in 2-methoxyethanol, followed by chromatography on basic alumina with an acetonitrile/methanol gradient, yielded 2cy as a pure yellow powder (0.209 g, 68%). $^1$H NMR (CDCl$_3$): δ=8.57 (d, 1H, J=7.3 Hz), 8.56 (d, 1H, J=8.6 Hz), 8.48 (d, 1H, J=8.2 Hz), 7.68 (t, 1H, J=7.9 Hz), 7.23 (d, 1H, J=8.2 Hz), 4.57 (t, 1H, J=3.6 Hz), 4.17 (t, 2H, J=7.6 Hz), 3.85 (m, 1H), 3.74 (m, 1H), 3.49 (m, 1H), 3.46 (t, 2H, J=6.4 Hz), 3.40 (m, 1H), 3.05 (s, 3H), 2.94 (t, 2H, J=6.3 Hz), 2.46 (s, 3H), 1.76 (m, 2H), 1.67 (m, 2H), 1.56 (m, 2H), 1.51 (m, 6H). $^{13}$C{$^1$H} NMR: δ=164.7, 164.2, 156.8, 132.5, 131.3, 130.9, 130.3, 126.4, 125.6, 123.4, 116.2, 115.3, 98.9, 67.6, 62.4, 56.6, 49.4, 42.1, 40.4, 36.8, 30.9, 29.7, 28.2, 25.7, 24.1, 19.8. ESI/MS m/z 454 (M+H)$^+$.

N-(5'-Tetrahydropyranoxypentyl)-4-(N'-methylaminoethylamino)naphthalene-1,8-dicarboximide (2cz): This was prepared analogously to 2ay. The reaction of 1cx (0.613 g, 1.53 mmol), N-methyl-1,2-diaminoethane (0.672 mL, 7.62 mmol), and triethylamine (213 μL, 1.53 mmol) in 2-methoxyethanol, followed by chromatography on silica with a chloroform/methanol gradient, yielded 2cz as a pure yellow powder (0.380 g, 57%). $^1$H NMR (CDCl$_3$): δ=8.56 (d, 1H, J=7.7 Hz), 8.44 (d, 1H, J=8.4 Hz), 6.16 (d, 1H, J=8.1 Hz), 7.60 (t, 1H, J=7.8 Hz), 6.67 (d, 1H, J=8.4 Hz), 6.25 (br t, 1H, J=4.2 Hz), 4.58 (t, 1H, J=3.6 Hz), 4.16 (t, 2H, J=7.6 Hz), 3.85 (m, 1H), 3.74 (m, 1H), 3.49 (m, 1H), 3.43 (m, 1H), 3.06 (t, 2H, J=5.7 Hz), 2.52 (s, 3H), 1.78–1.66 (m, 6H), 1.53–1.49 (m, 6H). $^{13}$C{$^1$H} NMR: δ=164.9, 164.3, 149.8, 134.7, 131.3, 130.0, 126.5, 124.8, 123.3, 120.6, 110.4, 104.6, 98.9, 67.6, 62.4, 49.7, 42.0, 40.3, 36.1, 30.9, 29.7, 28.3, 25.7, 24.1, 19.8. ESI/MS m/z 440 (M+H)$^+$.

N-n-Butyl-4-(N'-methylaminoethylene-N"-benzylmethylamino)naphthalene-1,8-dicarboximide (Bu)(NI)(Me2en)(Bn): A solution of benzyl bromide (75.3 μL, 0.633 mmol) in 40 mL of THF was added dropwise over 30 min to a solution of 2ay (0.215 g, 0.633 mmol) and triethylamine (88.3 μL, 0.634 mmol) in 40 mL of THF, followed by stirring for 23 hours at ambient temperature. The solvent was removed under vacuum and purification carried out by chromatography on silica gel with a toluene/acetone gradient, yielding (Bu)(NI)(Meen)(Bn) as a pure yellow oil.(0.124 g, 46%). $^1$H NMR (CDCl$_3$): δ=8.55 (t, 1H, J=7.5 Hz), 8.51 (t, 1H, J=8.2 Hz), 8.44 (d, 1J=8.2 Hz), 7.60 (t, 1H, J=7.9 Hz), 7.27 (m, 5H), 7.12 (d, 1H, J=8.2 Hz), 4.17 (t, 2H, J=7.6 Hz), 3.52 (s, 2H), 3.47 (t, 2H, J=6.6 Hz), 3.01 (s, 3H), 2.74 (t, 2H, J=6.7 Hz), 2.32 (s, 3H), 1.72 (m, 2H), 1.45 (m, 2H), 0.98 (t, 3H, J=7.4 Hz). $^{13}$C{$^1$H} NMR: δ=164.7, 164.2, 156.7, 138.8, 132.5, 131.1, 130.3, 129.4, 129.0, 128.4, 127.3, 125.9, 125.1, 123.2, 115.4, 114.7, 62.9, 55.5, 54.7, 42.9, 41.6, 40.1, 30.4, 20.5, 14.0. ESI/MS m/z 430 (M+H)$^+$, 309 (M–NMeBn)$^+$.

N-(5'-Hydroxypentyl)-4-(N'-methylaminoethylene-N"-benzylmethylamino)naphthalene-1,8-dicarboximide (AP)(NI)(Meen)(Bn): A solution of 1bx (0.292 g, 0.919 mmol), N-benzyl-N-methyl-1,2-diaminoethane (0.413 g, 2.51 mmol), triethylamine (0.175 mL, 1.26 mmol) in 20 mL of 2-methoxyethanol was heated at reflux for 41 hours. After cooling to ambient temperature, 30 mL of water was added, the solution extracted with 3×30 mL diethyl ether, the organic layer dried with MgSO$_4$, and solvent removed under vacuum. The crude material was purified by chromatography on silica with ethyl acetate, yielding (AP)(NI)(Meen)(Bn) as a pure yellow powder (0.162 g, 40%). $^1$H NMR (CDCl$_3$): δ=8.54 (d, 1H, J=6.7 Hz), 8.38 (d, 1H, J=8.4 Hz), 8.03 (d, 1H, J=8.3 Hz), 7.59 (t, 1H, J=7.9 Hz), 7.35 (m, 4H), 7.27 (m, 1H), 6.57 (d, 1H, J=8.4 Hz), 6.22 (br, 1H), 4.15 (t, 2H, J=7.4 Hz), 3.65 (t, 2H, J=6.5 Hz), 3.61 (s, 2H), 3.36 (m, 2H), 2.82 (t, 2H, J=5.7 Hz), 2.35 (s, 3H), 2.05 (br, 1H), 1.76 (m, 2H), 1.65 (m, 2H), 1.48 (m, 2H). $^{13}$C{$^1$H} NMR: δ=164.9, 164.3, 149.7, 138.6, 134.7, 131.2, 129.9, 129.2, 128.7, 127.7, 126.4, 124.7, 123.1, 120.5, 110.1, 104.5, 62.9, 62.3, 54.4, 42.1, 40.2, 40.1, 32.6, 28.1, 23.4. ESI/MS m/z 446 (M+H)$^+$.

N-n-Butyl4-(N'-methylaminoethylene-N"-ArBmethylamino)naphthalene-1,8-dicarboximide (3ay): A solution of 2,2-dimethylpropane-1,3-diyl[o-(bromomethyl)phenyl]boronate (0.173 g, 0.611 mmol) in 30 mL of THF was added dropwise over 15 min to a solution of 2ay (0.207 g, 0.610 mmol) and triethylamine (85.0 μL, 0.610 mmol) in 30 mL of THF, followed by stirring for 2 hours at ambient temperature. The solvent was removed under vacuum and purification carried out by chromatography on basic alumina with an acetonitrile/methanol gradient, yielding (3ay) as a pure yellow powder (0.160 g, 55%). $^1$H NMR (CD$_3$OD): δ=8.47 (d, 1H, J=8.0 Hz), 8.43 (d, 1H, J=7.4 Hz), 8.34 (d, 1H, J=8.2 Hz), 7.70 (t, 1H, J=7.9 Hz), 7.49 (d, 1H, J=7.0 Hz), 7.33 (d, 1H, J=8.2 Hz), 7.20 (t, 1H, J=6.9 Hz), 7.16 (dt, 1H), J=1.1 Hz, J=7.4 Hz), 7.07 (d, 1H, J=7.3 Hz), 4.03 (t, 4H, J=7.5 Hz), 3.71 (t, 2H, J=7.9 Hz), 3.27 (br, 2H), 3.05 (s, 3H), 2.55 (s, 3H), 1.63 (m, 2H), 1.39 (m, 2H), 0.97 (t, 3H, J=7.4 Hz). $^{13}$C{$^1$H} NMR (CD$_3$OD): δ=165.8, 165.4, 157.5, 139.8, 133.7, 133.5, 132.3, 132.2, 131.2, 128.4, 127.6, 127.3, 126.9, 124.2, 118.3, 117.2, 116.9,.64.5, 54.2, 52.1, 43.9, 42.1, 41.1, 31.4, 21.5, 14.4. ESI/MS m/z 474 (M+H)$^+$.

N-n-Butyl-4-(N'-aminoethylene-N"-ArBmethylamino)naphthalene-1,8-dicarboximide (3az): The procedure is analogous to that for the synthesis of 3ay. The reaction of 2,2-dimethylpropane-1,3-diyl[o-(bromomethyl)phenyl]boronate (0.280 g, 0.990 mmol), 2az (0.324 g, 0.996 mmol), and triethylamine (0.138 mL, 0.990 mmol) in THF, followed by chromatography on basic alumina with an acetonitrile/methanol gradient, yielded (3az) as a pure orange-yellow powder (0.385 g, 74%). These conditions gave 3az and the neopentylglycol-protected boronate ester. $^1$H NMR (CD$_3$OD): δ=8.64 (d, 1H, J=8.3 Hz), 8.46 (d, 1H, J=7.6 Hz), 8.29 (d, 1H, J=8.6 Hz), 7.61 (d, 1H, J=7.8 Hz), 7.58 (d, 1H, J=7.6 Hz), 7.24–7.17 (m, 3H), 6.82 (d, 1H, J=8.6 Hz), 4.19 (2H), 4.08 (t, 2H, J=7.5 Hz), 3.84 (t, 2H, J=6.1 Hz), 3.40 (br, 2H), 3.35 (s, 2H), 2.59 (s, 3H), 1.66 (m, 2H), 1.42 (m, 2H), 0.98 (t, 3H, J=6.1 Hz). $^{13}$C{$^1$H} NMR (CD$_3$OD): δ=166.3, 165.8, 152.1, 135.9, 134.5, 132.4, 131.2, 130.0, 129.4, 128.6, 128.3, 125.8, 123.5, 122.3, 110.5, 105.3,64.5, 56.1, 41.3,41.0,39.6, 31.5,21.5, 14.4. ESI/MS m/z 460 (M+H)$^+$.

N-(5'-Tetrahydropyranoxypentyl)-4-(N'-methylaminoethylene-N"-ArBmethylamino)naphthalene-1,8-dicarboximide (3cy). The procedure is analogous to that for the synthesis of 3ay. The reaction of 2,2-dimethylpropane-1,3-diyl[o-(bromomethyl)phenyl]boronate (0.150 g, 0.530 mmol), 2cy (0.241 g, 0.531 mmol), and triethylamine (74.1 μL, 0.532 mmol) in THF, followed by chromatography on neutral alumina with an acetonitrile/methanol gradient, yielded (3cy) as a pure yellow powder (0.218 g, 70%). $^1$H NMR (CD$_3$OD): δ=8.34 (d, 1H, J=8.4 Hz), 8.26 (d, 1H, J=7.2 Hz), 8.17 (d, 1H, J=8.1 Hz), 7.57 (t, 1H, J=7.8 Hz), 7.48 (d, 1H, J=7.0 Hz), 7.21–7.13 (m, 3H), 7.07 (d, 1H, J=7.2 Hz), 4.49 (s, 1H), 4.01 (br, 2H), 3.91 (t, 2H, J=7.4 Hz), 3.75 (m, 1H), 3.65 (m, 3H), 3.01 (s, 3H), 2.53 (s, 3H), 1.61 (m, 1H), 1.58 (m, 5H), 1.38 (m, 6H). $^{13}$C{$^1$H} (CD$_3$OD) NMR: δ=165.4, 164.9, 157.4, 140.0, 133.6, 133.3, 132.0, 131.0, 128.4, 128.3, 127.2, 127.0, 126.7, 123.9, 116.8, 116.5, 100.1, 68.3, 64.5, 63.2, 54.3, 52.2, 50.0, 43.7, 42.2, 41.1, 31.9, 30.5, 28.9, 26.7, 24.9, 20.6. ESI/MS m/z 588 (M+H)$^+$.

N-(5'-Tetrahydropyranoxypentyl)-4-(N'-aminoethylene-N"-ArBmethylamino)naphthalene-1,8-dicarboximide (3cz). The procedure is analogous to that for the synthesis of 3ay. The reaction of 2,2-dimethylpropane-1,3-diyl[o-(bromomethyl)phenyl]boronate (2.30 g, 8.15 mmol), 2cz (3.58 g, 8.15 mmol), and triethylamine (1.14 mL, 8.15 mmol) in THF yielded an orange oil after removal of the solvent under vacuum. Chromatography on silica with a gradient from 100% methanol to 10% ammonium hydroxide/methanol gave 3cz in the second band as a pure yellow powder (2.66 g, 57%). $^1$H NMR (CD$_3$OD): δ=8.72 (d, 1H, J=8.3 Hz), 8.52 (d, 1H, J=7.6 Hz), 8.36 (d, 1H, J=8.5

Hz), 7.66 (t, 1H, J=7.9 Hz), 7.59 (d, 1H, J=6.8 Hz), 7.24–7.16 (m, 3H), 6.89 (d, 1H, J=8.6 Hz), 4.56 (t, 1H, J=3.4 Hz), 4.20 (br, 2H), 4.13 (t, 2H, J=7.3 Hz), 3.86 (t, 2H, J 6.2 Hz), 3.80 (m, 1H), 3.72 (m, 1H), 3.41 (m, 4H), 3.35 (s, 2H), 2.60 (s, 3H), 1.74 (m, 3H), 1.65 (m, 3H), 1.48 (m, 6H). $^{13}C\{^{1}H\}$ NMR: δ=ESI/MG m/z 574 (M+H)$^{+}$.

N-(5'-Hydroxypentyl)4-(N'-aminoethylene-N"-ArBmethylamino)naphthalene-1,8-dicarboximide (3bz). Standard THP deprotection conditions were used. A solution of Ph$_3$PBr$_2$ (4.03 g, 9.55 mmol) in 10 mL of CH$_2$Cl$_2$ was added dropwise over 30 min to a solution of 3cz (2.61 g, 4.55 mmol) in 100 mL of CH$_2$Cl$_2$ at 0° C. to give a cloudy yellow mixture. After stirring at 0° C. for 2 hours, 30 mL of H$_2$O was added to precipitate an orange oil. The reaction was stirred at ambient temperature for 2 hours, followed by the removal of solvent under vacuum. Chromatography on silica gel using gradient elution with 100% methanol to 10% ammonium hydroxide/methanol gave 3bz yielded an orange oil after removal of the solvent under vacuum. Chromatography on silica with a gradient from 100% methanol to 10% ammonium hydroxide/methanol gave 3cz in the second band as a pure yellow powder (1.89 g, 85%). $^{1}H$ NMR (CD$_3$OD): δ=$^{13}C\{^{1}H\}$ NMR: δ=. ESI/MS m/z 490.1 (M+H)$^{+}$.

The foregoing written description is considered to be sufficient to enable one skilled in the art to practice the invention. The present invention is not to be limited in scope by the example presented herein. Indeed, various modifications of the invention in addition to those shown and described herein will become apparent to those skilled in the art from the foregoing description and fall within the scope of the appended claims.

What is claimed is:

1. A method of making a fluorescent compound that emits a signal that can be correlated to an analyte concentration, wherein the compound has the general formula:

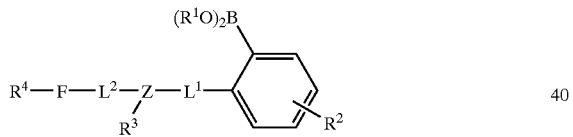

wherein R$^1$ is selected form the group consisting of hydrogen, lower aliphatic and aromatic functional groups;

wherein R$^2$ and R$^4$ are optional functional selected from the group consisting of hydrogen, lower aliphatic and aromatic functional groups and groups that form covalent bonds to a polymer matrix;

wherein L$^1$ and L$^2$ are optional linking groups having from zero to four atoms selected from the group consisting of nitrogen, carbon, oxygen, sulfur, and phosphorus;

wherein Z is a heteroatom selected from the group consisting of nitrogen, sulfur, oxygen and phosphorus;

wherein R$^3$ is an optional group selected from the group consisting of hydrogen, lower aliphatic and aromatic functional groups and groups that form covalent bonds to a polymer matrix;

wherein F is a fluorophore with selected molecular properties; the method comprising selecting F and Z to satisfy the following equation such that ΔG, the free energy for electron transfer, is less than about 3.0 kcal mol$^{-1}$:

$$\Delta G=23.06[E^0(Z^{oxidation})-E^0(F^{reduction})]-\Delta E_{00}],$$

wherein $E^0(Z^{oxidation})$ is the oxidation potential of Z, $E^0(F^{reduction})$ is the reduction potential of F, and ΔE00 is the energy of F in the excited state.

2. A method of identifying a fluorescent compound having substituents with complimentary molecular properties, wherein the compound has the general formula:

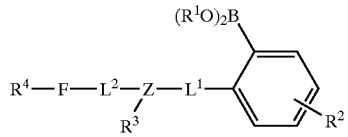

wherein R$^1$ is selected from the group consisting of hydrogen, lower aliphatic and aromatic functional groups;

wherein R$^2$ and R$^4$ are optional functional selected from the group consisting of hydrogen, lower aliphatic and aromatic functional groups and groups that form covalent bonds to a polymer matrix;

wherein L$^1$ and L$^2$ arc optional linking groups having from zero to four atoms selected from the group consisting of nitrogen, carbon, oxygen, sulfur, and phosphorus;

wherein Z is a heteroatom selected from the group consisting of nitrogen, sulfur, oxygen and phosphorus;

wherein R$^3$ is an optional group selected from the group consisting of hydrogen, lower aliphatic and aromatic functional groups and groups that form covalent bonds to a polymer matrix;

wherein F is a fluorophore with selected molecular properties; the method comprising determining whether F and Z satisfy the following equation such tat ΔG, the free energy for electron transfer, is less than about 3.0 kcal mol$^{-1}$:

$$\Delta G=23.06[E^0(Z^{oxidation})-E^0(F^{reduction})]-\Delta E_{00}],$$

wherein $E^0(Z^{oxidation})$ is the oxidation potential of Z, $E^0(F^{reduction})$ is the reduction potential of F, and ΔE$_{00}$ is the energy of F in the excited state.

3. The method as recited in claim 1, wherein F emits at a wavelength greater than about 500 nm.

4. The method as recited in claim 1, wherein F emits at a wavelength greater than about 550 nm.

5. The method as recited in claim 1, wherein F emits at a wavelength greater than about 600 nm.

6. The method as recited in claim 1, wherein the excitation wavelength for F is greater than about 400 nm.

7. The method as recited in claim 1, wherein the excitation wavelength for F is greater than about 450 nm.

8. The method as recited in claim 1, wherein F is selected from the group consisting of transition metal-ligand complexes, oxazines, oxazine-ones, oxazones, thiazines and anthracenes.

9. The method as recited in claim 8, wherein F comprises an oxazine-one boronate.

10. The method as recited in claim 1, wherein F comprises an anthracene-boronate.

11. The method as recited in claim 1, wherein F comprises a transition metal-ligand complex comprising a metal selected from the group consisting of ruthenium and chromium.

12. The method as recited in claim 1, wherein Z is nitrogen.

13. The method as recited in claim 1, wherein the fluorescent compound emits a signal that is correlated with the concentration of glucose.

14. The method as recited in claim 2, wherein F emits at a wavelength greater than about 500 nm.

15. The method as recited in claim 2, wherein F emits at a wavelength greater than about 550 nm.

16. The method as recited in claim 2, wherein F emits at a wavelength greater than about 600 nm.

17. The method as recited in claim 2, wherein the excitation wavelength for F is greater than about 400 nm.

18. The method as recited in claim 2, wherein the excitation wavelength for F is greater than about 450 nm.

19. The method as recited in claim 2, wherein F is selected from the group consisting of transition metal-ligand complexes, oxazines, oxazine-ones, oxazones, thiazines and anthracenes.

20. The method as recited in claim 19, wherein F comprises an oxazine-one boronate.

21. The method as recited in claim 19, wherein F comprises an anthracene-boronate.

22. The method as recited in claim 2, wherein F comprises a transition metal-ligand complex comprising a metal selected from the group consisting of ruthenium and chromium.

23. The method as recited in claim 2, wherein Z is nitrogen.

24. The method as recited in claim 2, wherein the fluorescent compound emits a signal that is correlated with the concentration of glucose.

* * * * *